(12) United States Patent
Hu et al.

(10) Patent No.: US 12,042,669 B2
(45) Date of Patent: Jul. 23, 2024

(54) SYSTEMS AND METHODS FOR MOTION TRACKING IN RADIATION THERAPY

(71) Applicant: SHANGHAI UNITED IMAGING HEALTHCARE CO., LTD., Shanghai (CN)

(72) Inventors: Lingzhi Hu, Houston, TX (US); Hongdi Li, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 422 days.

(21) Appl. No.: 17/348,740

(22) Filed: Jun. 15, 2021

(65) Prior Publication Data

US 2021/0308490 A1    Oct. 7, 2021

Related U.S. Application Data

(63) Continuation-in-part of application No. 16/455,869, filed on Jun. 28, 2019, now Pat. No. 11,707,235.

(30) Foreign Application Priority Data

May 8, 2019   (CN) .......................... 201910378793.3

(51) Int. Cl.
A61B 5/00     (2006.01)
A61B 5/33     (2021.01)
(Continued)

(52) U.S. Cl.
CPC .............. *A61N 5/1067* (2013.01); *A61B 5/33* (2021.01); *A61N 5/1049* (2013.01);
(Continued)

(58) Field of Classification Search
CPC .... A61N 2005/1055; A61N 2005/1059; A61N 5/1049; A61N 5/1068; A61N 5/33;
(Continued)

(56) References Cited

U.S. PATENT DOCUMENTS

2004/0010210 A1   1/2004 Avinash et al.
2008/0031406 A1   2/2008 Yan et al.
(Continued)

FOREIGN PATENT DOCUMENTS

CN    103315739 A    9/2013
CN    103584919 A    2/2014
(Continued)

OTHER PUBLICATIONS

Christoph Bert M.S. et al., Clinical Experience with a 3D Surface Patient Setup System for Alignment of Partial-breast Irradiation Patients, Int. J. Radiation Oncology Biol. Phys., 64 (4): 1265-1274, 2006.
(Continued)

*Primary Examiner* — Joel F Brutus
(74) *Attorney, Agent, or Firm* — METIS IP LLC

(57) ABSTRACT

A system for radiation therapy may obtain a plurality of sets of motion data each of which corresponds to one of a plurality of motion phases of a subject. A set of motion data corresponding to a motion phase may include first physiological motion data and second physiological motion reflecting a physiological motion during the motion phase. The first physiological motion data and the second physiological motion data may be collected via a medical imaging device and a first motion sensor, respectively. The system may also direct a radiotherapy device to deliver a radiation treatment to the subject according to a treatment plan. During the radiation treatment, the system may obtain target physiological motion data reflecting the physiological motion of the subject, the target physiological motion data being collected via a second motion sensor; and adjust the treatment plan to adapt to the physiological motion of the subject.

20 Claims, 16 Drawing Sheets

(51) Int. Cl.
  *A61N 5/10* (2006.01)
  *G01P 13/00* (2006.01)
  *G01R 33/54* (2006.01)
  *G01R 33/565* (2006.01)
  *G01R 33/567* (2006.01)
  *G01S 13/62* (2006.01)
  *G06T 11/00* (2006.01)

(52) U.S. Cl.
  CPC ............ *A61N 5/1068* (2013.01); *G01P 13/00* (2013.01); *G01R 33/543* (2013.01); *G01R 33/56509* (2013.01); *G01R 33/5673* (2013.01); *G01S 13/62* (2013.01); *G06T 11/003* (2013.01); *A61N 2005/1052* (2013.01); *A61N 2005/1055* (2013.01); *A61N 2005/1059* (2013.01); *G06T 2211/40* (2013.01)

(58) Field of Classification Search
  CPC .............. A61N 5/1067; G01R 33/5673; G01R 33/543; G01R 33/56509
  See application file for complete search history.

(56) References Cited

U.S. PATENT DOCUMENTS

| | | |
|---|---|---|
| 2009/0192384 A1 | 7/2009 | Fontius |
| 2009/0245457 A1 | 10/2009 | Takeuchi et al. |
| 2010/0172567 A1 | 7/2010 | Prokoski |
| 2010/0290683 A1 | 11/2010 | Demeester et al. |
| 2012/0169333 A1 | 7/2012 | Katscher et al. |
| 2013/0165770 A1* | 6/2013 | Li .................... A61N 5/1067 600/430 |
| 2013/0251225 A1 | 9/2013 | Liu et al. |
| 2015/0366527 A1 | 12/2015 | Yu et al. |
| 2017/0016972 A1 | 1/2017 | Bhat et al. |
| 2017/0206668 A1 | 7/2017 | Poulos et al. |
| 2017/0358095 A1 | 12/2017 | Levy |
| 2018/0289980 A1 | 10/2018 | Fredriksson et al. |
| 2018/0368721 A1 | 12/2018 | Ahn |
| 2019/0057521 A1* | 2/2019 | Teixeira ............... A61B 90/361 |
| 2019/0336795 A1 | 11/2019 | Zhou et al. |
| 2020/0126231 A1 | 4/2020 | Hu et al. |
| 2020/0352524 A1 | 11/2020 | Hu et al. |
| 2021/0059628 A1 | 3/2021 | Yang et al. |
| 2022/0248966 A1 | 8/2022 | Freeman et al. |

FOREIGN PATENT DOCUMENTS

| | | |
|---|---|---|
| CN | 103892813 A | 7/2014 |
| CN | 104569963 A | 4/2015 |
| CN | 106251380 A | 12/2016 |
| CN | 107730567 A | 2/2018 |
| CN | 109199346 A | 1/2019 |
| CN | 109363702 A | 2/2019 |
| JP | 5942244 B2 | 6/2016 |
| WO | 2010069168 A1 | 6/2010 |

OTHER PUBLICATIONS

Li, Changzhi et al., Radar Motion Sensing for Accurate Tumor Tracking in Radiation Therapy, WAMICON 2011 Conference Proceedings, 2011, 6 pages.

Joshua, Olick-Gibson et al., Feasibility Study of Surface Motion Tracking with Millimeter Wave Technology during Radiotherapy, Medical physics, 47(3): 1229-1237, 2020.

Nicholas J. Tustison et al., Explicit B-spline Regularization in Diffeomorphic Image Registration, Frontiers in Neuroinformatics, 2013, 13 pages.

F. Thiel et al., Combining Magnetic Resonance Imaging and Ultrawideband Radar: A New Concept for Multimodal Biomedical Imaging, Review of Scientific Instruments, 80(1): 014302-1-014302-10, 2009.

Stefano Pisa et al., A Survey of Radar Systems for Medical Applications, IEEE Aerospace and Electronic Systems Magazine, 31(11): 64-81, 2016.

F. Thiel et al., Non-contact Detection of Myocardium's Mechanical Activity by Ultrawideband RF-radar and Interpretation Applying Electrocardiogramaview of Scientific Instruments, 80(11): 114302-1-114302-12, 2009.

* cited by examiner

1400

```
┌─────────────────────────────────────────────────────────────┐
│ Obtaining a plurality of sets of motion data each of which  │
│ corresponds to one of a plurality of motion phases of a     │
│ subject, a set of motion data corresponding to a motion     │
│ phase including first physiological motion data and second  │     1401
│ physiological motion reflecting a physiological motion      │
│ during the motion phase, the first physiological motion     │
│ data and the second physiological motion data being         │
│ collected via a medical imaging device and a first motion   │
│ sensor, respectively                                        │
└─────────────────────────────────────────────────────────────┘
                              │
                              ▼
┌─────────────────────────────────────────────────────────────┐
│ Directing a radiotherapy device to deliver a radiation       │     1402
│ treatment to the subject according to a treatment plan       │
└─────────────────────────────────────────────────────────────┘
                              │
                              ▼
┌─────────────────────────────────────────────────────────────┐
│ During the radiation treatment, obtaining target             │
│ physiological motion data reflecting the physiological       │     1403
│ motion of the subject, the target physiological motion       │
│ data being collected via a second motion sensor              │
└─────────────────────────────────────────────────────────────┘
                              │
                              ▼
┌─────────────────────────────────────────────────────────────┐
│ During the radiation treatment, adjusting the treatment      │
│ plan to adapt to the physiological motion of the subject     │     1404
│ based on the target physiological motion data and the        │
│ plurality of sets of motion data                             │
└─────────────────────────────────────────────────────────────┘
```

```
┌─────────────────────────────────────────────────────────────┐
│ Obtaining target rigid motion data reflecting a rigid       │  1601
│ motion of a subject during a radiation treatment            │
└─────────────────────────────────────────────────────────────┘
                              │
                              ▼
┌─────────────────────────────────────────────────────────────┐
│ Correcting target surface motion data based on the target   │  1602
│ rigid motion data                                           │
└─────────────────────────────────────────────────────────────┘
                              │
                              ▼
┌─────────────────────────────────────────────────────────────┐
│ Adjusting a treatment plan to adapt to a physiological      │  1603
│ motion of the subject based on the corrected target surface │
│ motion data and a plurality of sets of motion data          │
└─────────────────────────────────────────────────────────────┘
```

┌─ 1701
Obtaining MRI data and sensor data that are simultaneously collected via an MRI device and a first motion sensor during an MRI scan of the subject, respectively, the sensor data relating to a physiological motion of the subject during the MRI scan

↓

┌─ 1702
Directing a radiotherapy device to deliver a radiation treatment to the subject according to a treatment plan

↓

┌─ 1703
During the radiation treatment, obtaining target sensor data relating to the physiological motion of the subject collected via a second motion sensor during the radiation treatment

↓

┌─ 1704
During the radiation treatment, adjusting the treatment plan to adapt to the physiological motion of the subject based on the target sensor data, the MRI data, and the sensor data

FIG. 17

SYSTEMS AND METHODS FOR MOTION TRACKING IN RADIATION THERAPY

CROSS-REFERENCE OF RELATED APPLICATION

This application is a Continuation-in-part of U.S. application Ser. No. 16/455,869, filed on Jun. 28, 2019, which claims priority of Chinese Patent Application No. 201910378793.3, filed on May 8, 2019, the contents of which are hereby incorporated by reference.

TECHNICAL FIELD

The present disclosure generally relates to radiation therapy, and more particularly, relates to systems and methods for motion tracking in radiation therapy.

BACKGROUND

Radiation therapy has been widely employed in cancer treatment in which a radiation beam is delivered toward a target (e.g., a tumor) of a subject (e.g., a patient). In radiation therapy, one or more regions of interest (ROIs), e.g., the target and/or an organ-at-risk (OAR) near the target, may move due to a physiological motion (e.g., a cardiac motion or a respiratory motion) of the subject, which may reduce the precision of the radiation delivery toward the target. Therefore, it is desirable to provide methods and systems for motion tracking in radiation therapy, thereby improving the precision of treatment delivery.

SUMMARY

An aspect of the present disclosure provides a system for radiation therapy. The system may comprise at least one storage device including a set of instructions and at least one processor configured to communicate with the at least one storage device. When executing the set of instructions, the at least one processor is configured to direct the system to perform operations. The system may obtain a plurality of sets of motion data each of which corresponds to one of a plurality of motion phases of a subject. A set of motion data corresponding to a motion phase may include first physiological motion data and second physiological motion data reflecting a physiological motion during the motion phase. The first physiological motion data and the second physiological motion data may be collected via a medical imaging device and a first motion sensor, respectively. The system may also direct a radiotherapy device to deliver a radiation treatment to the subject according to a treatment plan. During the radiation treatment, the system may obtain target physiological motion data reflecting the physiological motion of the subject during the radiation treatment, the target physiological motion data being collected via a second motion sensor; and adjust the treatment plan to adapt to the physiological motion of the subject based on the target physiological motion data and the plurality of sets of motion data.

Another aspect of the present disclosure provides a system for radiation therapy. The system may comprise at least one storage device including a set of instructions and at least one processor configured to communicate with the at least one storage device. When executing the set of instructions, the at least one processor may be configured to direct the system to perform operations. The system may obtain MRI data and sensor data that are simultaneously collected via an MRI device and a first motion sensor during an MRI scan of the subject, respectively. The sensor data may relate to a physiological motion of the subject during the MRI scan. The system may also direct a radiotherapy device to deliver a radiation treatment to the subject according to a treatment plan. During the radiation treatment, the system may further obtain target sensor data relating to the physiological motion of the subject collected via a second motion sensor during the radiation treatment; and adjust the treatment plan to adapt to the physiological motion of the subject based on the target sensor data, the MRI data, and the sensor data.

Another aspect of the present disclosure provides a system. The system may comprise a medical imaging device configured to acquire scan data of a subject by performing a medical scan on the subject before a radiation treatment of the subject; a first motion sensor configured to acquire sensor data relating to a physiological motion of the subject during the medical scan of the subject; a radiotherapy device configured to deliver the radiation treatment to the subject according to a treatment plan; a second motion sensor configured to acquire target sensor data relating to the physiological motion of the subject during the radiation treatment; and a processing device configured to adjust the treatment plan to adapt to the physiological motion of the subject during the radiation treatment based on the scan data, the sensor data, and the target sensor data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 14 is a flowchart illustrating an exemplary process for treating a subject according to some embodiments of the present disclosure;

FIG. 16 is a flowchart illustrating an exemplary process for adjusting a treatment plan according to some embodiments of the present disclosure;

FIG. 17 is a flowchart illustrating an exemplary process for treating a subject according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 2:
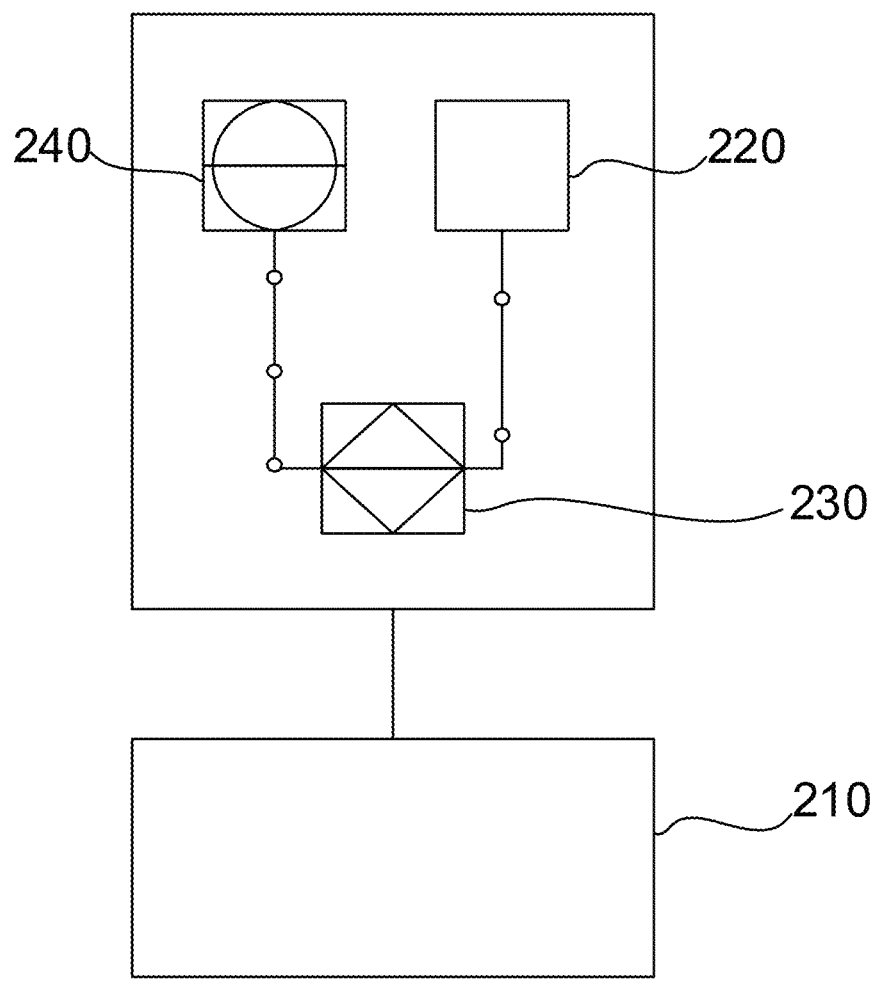
FIG. 2 is a schematic diagram illustrating an exemplary medical device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., a processing device 240 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Provided herein are systems and components for medical imaging and/or medical treatment (e.g., radiation treatment). In some embodiments, the medical systems may include one or more imaging modalities including Digital Subtraction Angiography (DSA), Magnetic Resonance Imaging (MRI), Magnetic Resonance Angiography (MRA), Computed tomography (CT), Computed Tomography Angiography (CTA), Ultrasound Scanning (US), Positron Emission Tomography (PET), Single-Photon Emission Computerized Tomography (SPECT), CT-MR, CT-PET, CE-SPECT, DSA-MR, PET-MR, PET-US, SPECT-US, TMS (transcranial magnetic stimulation)-MR, US-CT, US-MR, X-ray-CT, X-ray-MR, X-ray-portal, X-ray-US, Video-CT, Vide-US, or the like, or any combination thereof. In some embodiments, the medical systems may include a radiation treatment system, such as a three-dimensional conformal radiation therapy system, an intensity-modulated radiation therapy (IMRT) system, a volumetric modulated arc therapy (VMAT) system, an image guided radiotherapy (IGRT) system, a stereotactic radiosurgery system, a Gamma Knife radiosurgery system, a stereotactic body radiation therapy (SBRT) system, an intraoperative radiation therapy (IORT) system, etc.

An aspect of the present disclosure relates to systems and methods for controlling a medical device. The medical device may include a medical imaging device, e.g., an MRI device. In some embodiments, the systems may include one or more motion sensors, such as one or more radars, one or more cameras, etc. The medical device may be controlled by fusing data acquired by the one or more radars and the one or more cameras. For example, the systems may determine first data regarding a first motion of a subject by processing a plurality of image frames acquired by the one or more cameras. The systems may determine second data regarding second data regarding a second motion of the subject by processing radar echo data acquired by the one or more radars. The radar echo data may be corrected based on the first data. In some embodiments, the first motion may include a rigid motion of the subject, and the second motion may include a physiological motion. The systems may extract physiological motion information based on the first data and the second data. For example, the physiological motion information may include cardiac motion data and/or respiratory motion data. The systems may control, based on the physiological motion information, the medical device in order to reduce or avoid the effect of motion artifacts in, e.g., imaging, delivery of a treatment dosage (e.g., a radiation beam toward a target region).

Another aspect of the present disclosure provides systems and methods for motion tracking in radiation therapy. For example, the systems may obtain a plurality of sets of motion data each of which corresponds to one of a plurality of motion phases of a subject. A set of motion data corresponding to a motion phase may include first physiological motion data and second physiological motion reflecting a physiological motion during the motion phase, the first physiological motion data and the second physiological motion data being collected via a medical imaging device and a first motion sensor, respectively. The systems may also direct a radiotherapy device to deliver a radiation treatment to the subject according to a treatment plan. During the radiation treatment, the systems may obtain target physiological motion data reflecting the physiological motion of the subject, and adjust the treatment plan to adapt to the physiological motion of the subject based on the target physiological motion data and the plurality of sets of motion data. The target physiological motion data may be collected via a second motion sensor. In this way, the physiological motion of the subject may be tracked timely (e.g., in substantially real-time) and efficiently during the radiation treatment, and the treatment plan can be adjusted to adapt to the physiological motion of the subject during radiation treatment in a more timely and accurate manner.

Some embodiments of the present disclosure are provided with reference to a medical device that includes an imaging device (e.g., a scanner). However, it is understood that it is for illustration purposes only and not intended to limit the scope of the present disclosure. The systems and methods disclosed herein may be suitable for other applications. Merely by way of example, the medical device may include a radiotherapy device (an image guided radiotherapy (IGRT) device); the systems and methods for identifying a physiological motion may be used in controlling the delivery of a radiation beam in radiotherapy. Some embodiments of the present disclosure are provided with reference to motion tracking in a radiation treatment. However, it is understood that it is for illustration purposes only and not intended to limit the scope of the present disclosure. The systems and methods for motion tracking in a radiation treatment may be suitable for other applications, for example, used in motion tracking during a scan.

Figure 1:
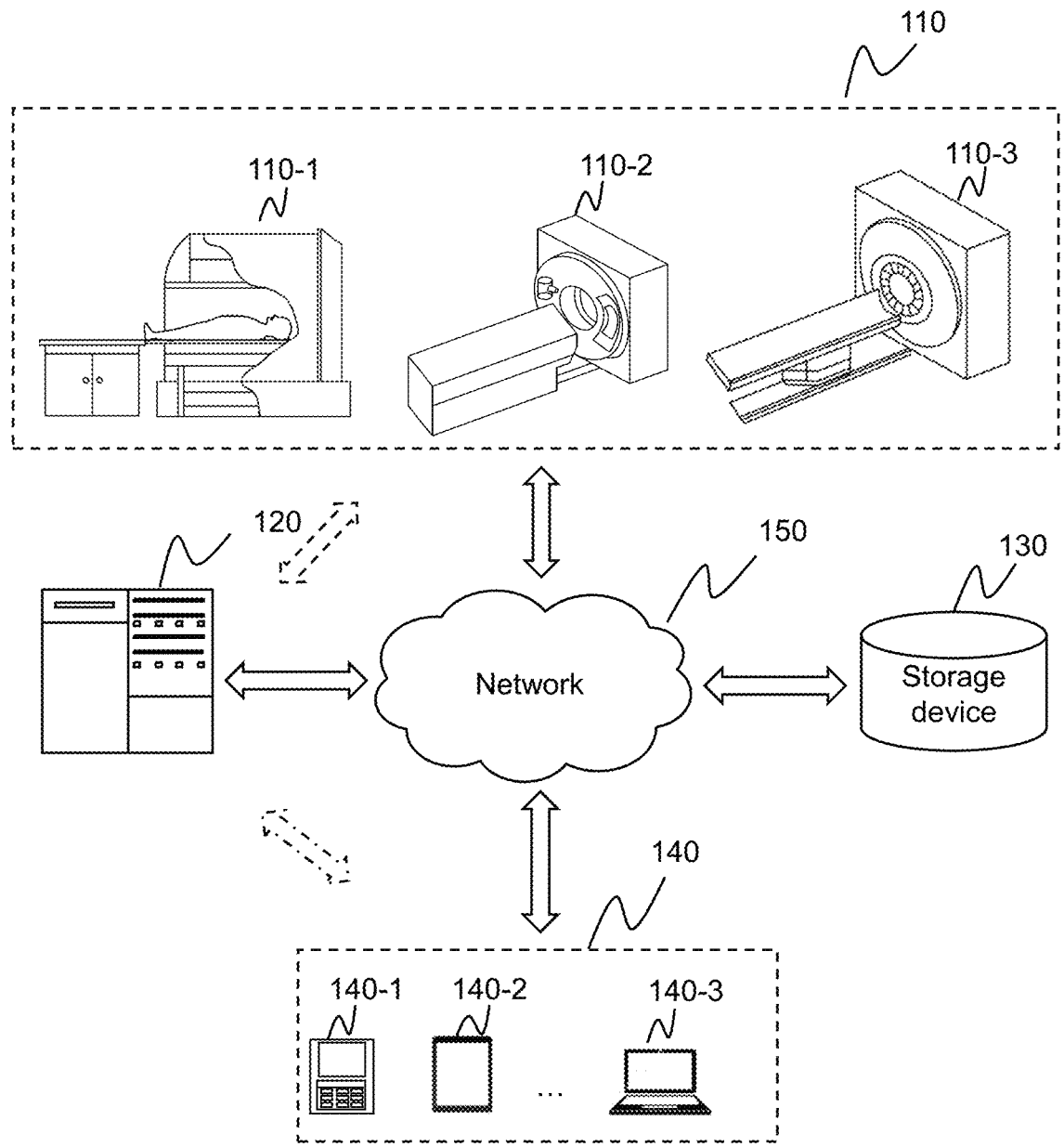
FIG. 1 is a schematic diagram illustrating an exemplary medical system according to some embodiments of the present disclosure.

FIG. 1 is a schematic diagram illustrating an exemplary medical system according to some embodiments of the present disclosure. As shown in FIG. 1, medical system 100 may include a medical device 110, a processing device 120, a storage device 130, one or more terminals 140, and a network 150. The components in the medical system 100 may be connected in one or more of various ways. Merely by way of example, as illustrated in FIG. 1, the medical device 110 may be connected to the processing device 120 through the network 150. As another example, the medical device 110 may be connected to the processing device 120 directly as indicated by the bi-directional arrow in dotted lines linking the medical device 110 and the processing device 120. As a further example, the storage device 130 may be connected to the processing device 120 directly or through the network 150. As still a further example, one or more terminals 140 may be connected to the processing device 120 directly (as indicated by the bi-directional arrow in dotted lines linking the terminal 140 and the processing device 120) or through the network 150.

In some embodiments, the medical device 110 may include a medical imaging device configured to generate or provide image data by scanning a subject or at least a part of the subject. Exemplary medical imaging devices may include a positron emission tomography (PET) device, a single photon emission computed tomography (SPECT) device, a computed tomography CT device, a magnetic resonance imaging (MRI) device, or the like, or any combination thereof. In some embodiments, the medical device 110 may include a single-modality scanner. The single-modality scanner may include, for example, a magnetic resonance imaging (MRI) scanner 110-1, a computed tomography (CT) scanner 110-2, and/or a positron emission tomography (PET) scanner 110-3. In some embodiments, the medical device 110 may include both the CT scanner 110-2 and the PET scanner 110-3. In some embodiments, image data of different modalities related to the subject, such as CT image data and PET image data, may be acquired using different scanners separately. In some embodiments, the medical device 110 may include a multi-modality scanner. The multi-modality scanner may include a positron emission tomography-computed tomography (PET-CT) scanner, a positron emission tomography-magnetic resonance imaging (PET-MRI) scanner, or the like, or any combination thereof. The multi-modality scanner may perform multi-modality imaging simultaneously. For example, the PET-CT scanner may generate structural X-ray CT image data and functional PET image data simultaneously in a single scan. The PET-MRI scanner may generate MRI data and PET data simultaneously in a single scan.

In some embodiments, the medical device 110 may include a radiation therapy (or radiotherapy) device. For example, the radiation therapy device may deliver one or more radiation beams to a treatment region (e.g., a tumor) of a subject (e.g., a patient) for causing an alleviation of the subject's symptom. In some embodiments, the RT device may be a conformal radiation therapy device, an image guided radiation therapy (IGRT) device, an intensity modulated radiation therapy (IMRT) device, an intensity modulated arc therapy (IMAT) device, or the like. For example, the medical device 110 may include an IGRT device (not shown in FIG. 1). Exemplary IGRT devices may include a positron emission tomography-radiotherapy (PET-RT) device, or a magnetic resonance imaging-radiotherapy (MRI-RT) device, etc.

In some embodiments, the radiation therapy device may include a linear accelerator (also referred to as "linac"). The linac may generate and emit a radiation beam (e.g., an X-ray beam) from a treatment head. The radiation beam may pass through one or more collimators (e.g., a multi-leaf collimator) forming certain shapes, and enter into the subject. In some embodiments, the radiation beam may include electrons, photons, or other types of radiation. In some embodiments, the energy of the radiation beam may be in the megavoltage range (e.g., >1 MeV), and may therefore be referred to as a megavoltage beam. The treatment head may be coupled to a gantry. The gantry may rotate, for example, clockwise or counterclockwise around a gantry rotation axis. In some embodiments, the treatment head may rotate along with the gantry. In some embodiments, the radiation therapy device may further include a table configured to support the subject during radiation treatment.

In some embodiments, the subject may include a body, a substance, or the like, or any combination thereof. In some embodiments, the subject may include a specific portion of a body, such as a head, a thorax, an abdomen, or the like, or any combination thereof. In some embodiments, the subject may include a specific organ, such as an esophagus, a trachea, a bronchus, a stomach, a gallbladder, a small intestine, a colon, a bladder, a ureter, a uterus, a fallopian tube, etc. In some embodiments, the subject may include a physical model (e.g., a water phantom). In the present disclosure, "object" and "subject" are used interchangeably. In some embodiments, the medical device 110 may include a scanning table. The subject may be placed on the scanning table for imaging.

In some embodiments, the medical device 110 may transmit collected data (e.g., image data) via the network 150 to the processing device 120, the storage device 130, and/or the terminal(s) 140. For example, the image data may be sent to the processing device 120 for further processing, or may be stored in the storage device 130. In some embodiments, the medical device 110 may be configured to scan the subject or at least a part of the subject in response to a control signal generated by the processing device 120.

The processing device 120 may process data and/or information obtained from the medical device 110, the storage device 130, and/or the terminal(s) 140. For example, the processing device 120 may obtain first data regarding a first motion of the subject through one or more cameras disposed in the medical device 110. The processing device 120 may obtain second data regarding a second motion of the subject through one or more radars disposed in the medical device 110. The processing device 120 may generate a control signal based on the first data and the second data. As another example, the processing device 120 may generate an image (e.g., an MR image) by reconstructing scan data acquired by the medical device 110 (e.g., an MRI device). As yet another example, during a radiation treatment of the subject, the processing device 120 may track a physiological motion of the subject and adjust a treatment plan of the radiation treatment to adapt to the physiological motion of the subject.

In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, and/or the terminal(s) 140 via the network 150. As another example, the processing device 120 may be directly connected to the medical device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage device 130 may store data, instructions, and/or any other information. In some embodiments, the storage device 130 may store data obtained from the medical device 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140, etc.). One or more components in the medical system 100 may access the data or instructions stored in the storage device 130 via the network 150. In some embodiments, the storage device 130 may be part of the processing device 120.

The terminal(s) 140 may be connected to and/or communicate with the medical device 110, the processing device 120, and/or the storage device 130. For example, the terminal(s) 140 may obtain a processed image from the processing device 120. As another example, the terminal(s) 140 may obtain scan data acquired by the medical device 110 and transmit the scan data to the processing device 120 to be processed. In some embodiments, the terminal(s) 140 may include a mobile device 140-1, a tablet computer 140-2, a laptop computer 140-3, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate exchange of information and/or data for the medical system 100. In some embodiments, one or more components of the medical system 100 (e.g., the medical device 110, the processing device 120, the storage device 130, the terminal(s) 140, etc.) may communicate information and/or data with one or more other components of the medical system 100 via the network 150. For example, the processing device 120 may obtain image data from the medical device 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 130 may be a data storage including cloud computing platforms, such as, a public cloud, a private cloud, a community cloud, and a hybrid cloud, etc. However, those variations and modifications do not depart from the scope of the present disclosure.

In some embodiments, the medical system 100 may further include one or more motion sensors configured to collect sensor data, which may include or be used to determine physiological motion data of the subject. The physiological motion data may include a physiological signal (e.g., an ECG signal, a respiratory signal) of the subject. Additionally or alternatively, the physiological motion data may include surface motion data reflecting a surface motion of the subject, wherein the surface motion may be induced by the physiological motion of the subject. Exemplary motion sensors may include a radar sensor (e.g., a radar 220 as described in connection with FIG. 2), an optical sensor, a ranging device, a time-of-flight (TOF) device, a structured light scanner, a camera (e.g., a camera 230 as described in connection with FIG. 2), a cardiac sensor (e.g., an ECG sensor), a respiratory sensor, or the like, or any combination thereof. Exemplary sensor data collected by the motion sensor(s) may include image data, position data, depth data, point-cloud data, radar echo data (which will be described in detail in connection with FIG. 2), a physiological signal, or the like, or any combination thereof. For example, the motion sensor(s) may include an optical sensor, a camera (e.g., a digital camera, an analog camera, etc.), a red-green-blue (RGB) sensor, an RGB-depth (RGB-D) sensor, or another device that can capture image data of the subject. As another example, the motion sensor(s) may include devices, such as a 3D laser imaging device, a structured light scanner (e.g., a structured light laser scanner) that can acquire point-cloud data of the subject. The point-cloud data may include a plurality of data points, each of which may represent a physical point on a body surface of the subject and can be described using one or more feature values of the physical point (e.g., feature values relating to the position and/or the composition of the physical point). As yet another example, the motion sensor(s) may include a device capable of acquiring position data and/or depth data of the subject, such as, a structured light scanner, a time-of-flight (TOF) device, a stereo triangulation camera, a sheet of light triangulation device, an interferometry device, a coded aperture device, a stereo matching device, or the like, or any combination thereof.

In some embodiments, surface motion data collected via a motion sensor may reflect a surface motion of the subject. The surface motion of the subject may be induced by a physiological motion inside the subject. Merely by way of example, the cardiac motion and/or the respiratory motion of the subject may result in a surface motion of the body surface at the chest and the abdomen of the subject. In some embodiments, the surface motion data collected via the motion sensor may be used to determine or estimate data relating to a physiological motion of the subject. For example, radar echo data collected by a radar sensor may be used to determine second data relating to a physiological motion of the subject (e.g., cardiac motion data and/or respiratory motion data) as described elsewhere in this disclosure (e.g., FIGS. 14, 15, and the relevant descriptions).

For the convenience of descriptions, data related to a physiological motion of the subject determined based on the sensor data collected via a motion sensor is referred to as second physiological motion data or sensor-based physiological motion data. In some embodiments, the second physiological motion data may be determined based on sensor data by the motion sensor itself (e.g., a processor of the motion sensor) or another computing device (e.g., the processing device 120). In some embodiments, the second physiological motion data collected via a motion sensor may be used for physiological motion tracking during a scan or a radiation treatment performed on the subject. More descriptions regarding the physiological motion tracking may be found elsewhere in the present disclosure. See, e.g., FIG. 14 and relevant descriptions thereof.

In some embodiments, a motion sensor may be configured to collect sensor data before or during a scan or a treatment of the subject. For example, the motion sensor may be directed to collect sensor data of the subject (or a portion thereof) during a radiation treatment continuously or intermittently (e.g., periodically) so that surface motion of the subject (or a portion thereof) may be tracked in real-time or intermittently. In some embodiments, the motion sensor may move to different positions, e.g., with a rotation of a gantry of the medical device 110, to collect sensor data from different perspectives during the radiation treatment. Alternatively, the motion sensor may be placed at a fixed position to collect sensor data from a fixed perspective in the radiation treatment.

In some embodiments, a motion sensor may be detachably mounted on the medical device 110 (e.g., the gantry, the table). For example, the medical device 110 may include a plurality of motion sensors which are arranged in a ring design around the detection tunnel formed by the gantry. During a radiation treatment, all of the motion sensors may be actuated to collect sensor data of the subject from their respective perspectives. Alternatively, a portion of the motion sensors close to an ROI of the subject may be actuated to collect sensor data relating to the ROI.

In some embodiments, a motion sensor may be mounted on the gantry via a retractable and/or movable mechanism. The position of the motion sensor may be adjusted by the retractable and/or movable mechanism. For example, the motion sensor may be placed at a desired position by the retractable and/or movable mechanism during a radiation treatment to avoid that beams traverse the motion sensor before entry into the subject. In some embodiments, the motion sensor may share the same gantry as a treatment radiation source. Alternatively, the motion sensor and the treatment radiation source may be mounted on different gantries.

FIG. 2 is a schematic diagram illustrating an exemplary medical device according to some embodiments of the present disclosure. As shown in FIG. 2, medical device 200 may include a scanner 210, one or more radars 220, one or more cameras 230, and a processing device 240. The scanner 210 may be configured to scan a subject or at least a part of the subject, and acquire corresponding scan data. The one or more radars 220 may be configured to acquire radar echo data from the subject. In some embodiments, the radar echo data may include data related to a physiological motion of the subject (hereinafter physiological motion related data). In some embodiments, the radar echo data may include the physiological motion related data and data related to a rigid motion of the subject (hereinafter rigid motion related data). The one or more cameras 230 may be configured to acquire a plurality of image frames of the subject. In some embodiments, the rigid motion may be identified based on at least a part of the plurality of image frames. The processing device 240 may be configured to process data/signals acquired by the one or more cameras 230 and the one or more radars 220 (e.g., image data and radar echo data), and generate a control signal for controlling the scanner 210 to scan the subject. In some embodiments, the processing device 240 may be configured to reconstruct an image based on the scan data. In some embodiments, the one or more radars 220 and the one or more cameras 230 may be exemplary embodiments of a motion sensor as described elsewhere in this disclosure (e.g., FIGS. 1, 14, and the relevant descriptions).

In some embodiments, the scanner 210 may include a CT device, an MRI device, a PET device, an ultrasonic device, an X-ray imaging device, or the like. In some embodiments, the medical device 220 may include a treatment device, e.g., a radiation treatment device, instead of the scanner 210. For example, the medical device 200 may be the IGRT device. The following description is provided with reference to exemplary embodiments that the medical device includes a scanner 210 for illustration purposes and not intended to be limiting.

The scanner 210 may include various suitable medical imaging devices for diagnosing and/or treating a disease, and not intended to be limiting. Taking the MRI device as an example, a magnetic resonance unit of the MRI device may include a magnet assembly, a gradient coil assembly, and a radiofrequency (RF) coil assembly. For example, the magnet assembly may generate a main magnetic field for polarizing the subject to be scanned. The gradient coil assembly may generate a gradient magnetic field. The RF coil assembly may include a plurality of RF coils for transmitting and/or receiving RF signals. In some embodiments, the magnetic resonance unit may form a cavity providing an examination space. The scanning table may move along the cavity. The subject may be placed on the scanning table for MR imaging.

In some embodiments, a radar of the one or more radars 220 may at least include an antenna and a processing component. In some embodiments, the antenna and the processing component may be integrated into a single chip. In some embodiments, the antenna and the processing component may be disposed separately. In some embodiments, the antenna may transmit radar signals to the subject within a coverage zone in a radar field. The antenna may receive radar echo signals reflected from the subject within the coverage zone. In some embodiments, a radar may include multiple antennas. The detection angle of the antenna may be adjusted according to the position of the subject or at a part of the subject. For example, a detectable region of the multiple antennas may be designed to cover the subject at suitable detection angles (e.g., 60 degrees, 70 degrees, 130 degrees, or 180 degrees) in order to acquire large-scale radar echo data. As another example, a detection region of at a part of the multiple antennas may be designed to cover a region of interest (ROI) of the subject in order to acquire radar echo data regarding the ROI (e.g., a thoracic and abdominal region). In some embodiments, the detection angle of the antenna may be a fixed angle (e.g., 60 degrees). In some embodiments, the radar may be a phased array radar having an antenna array forming by a plurality of antenna units. Each antenna unit may be controlled by a single phase shift switch. The phase beams may be synthesized by controlling the phase beam emitted by each antenna unit.

In some embodiments, the one or more radars 220 may be used to provide a non-invasive remote monitoring for the physiological motion. The one or more radars 220 may be disposed on various suitable positions for monitoring the physiological motion. For example, the one or more radars 220 may be disposed on a component of the scanner 210, such as, on an RF receiving coil, in a cavity around the examination space, or on a scanning table. As another example, the one or more radars 220 may be attached to the subject's clothes (e.g., the position close to the thoracic and abdominal region). In some embodiments, the one or more radars 220 may be disposed on a suitable position outside the medical device, such as, on a ceiling of a treatment room, on the floor of the treatment room, or a holder outside the medical device, etc.

In some embodiments, a distance between a radar and the subject may be 0-25 meters (e.g., less than 5 meters). Alternatively, the distance may be 1 millimeter to 3 meters, such as, 1 meter, or 2 meters. Alternatively, the distance may be 10 millimeters to 3000 millimeters, such as 100 millimeters to 2000 millimeters. The radar may emit radar beams (e.g., electromagnetic waves) to irradiate the subject, and receive radar echo signals reflected by the subject. In some embodiments, an emission frequency of the radar may be set as 1 GHz to 100 GHz. For example, a low-frequency range (e.g., 1 GHZ to 50 GHZ) may be used to detect an interior movement inside the subject (e.g., a cardiac movement, a diaphragm movement). A high-frequency range of the radar (e.g., 50 GHz to 100 GHz) may be used to detect a body surface movement (e.g., a skin movement). In some embodiments, the emission frequency of the radar may be set as different frequency ranges so as to identify various movements regarding the subject.

In some embodiments, the one or more radars 220 may include a single-mode radar and/or a multi-mode radar. For example, the single-mode radar may include a continuous wave (CW) radar, a non-continuous wave radar (e.g., an ultra-wideband (UWB) radar, or a frequency modulated continuous wave (FMCW) radar), a LIDAR, and so on. The multi-mode radar may include a CW-UWB radar, a CW-FMCW radar, or a UWB-FMCW radar, and so on. The types of the radar may be adjusted according to different scenarios. For example, the CW radar may be activated to monitor the cardiac motion. As another example, the UWB radar may be activated to monitor the abdominal movement. As a further example, a combined use of the CW radar and the UWB radar may be used to detect the radiation in various wavebands (e.g., in the millimeter wavelength range) that is emitted or reflected by the subject.

In some embodiments, the one or more radars 220 may be configured to detect radar echo signals from the subject. The radar echo signals may include motion information regarding the subject (e.g., rigid motion information and/or physiological motion information). For example, the rigid motion may include a translational and/or rotational motion of the subject. Exemplary rigid motions may include a pose motion of the subject, such as the rotating or nodding of the head of the subject, legs motion, hands motion, and so on. As another example, the physiological motion may include respiratory motion (or breathing motion), heart motion (or cardiac motion), and so on. In some embodiments, the radar echo signals may be image data or point cloud data. For example, the radar echo signals may be three-dimensional image data regarding the head of the subject. As another example, the radar echo signals may be point cloud data including location information of one or more characteristic points (e.g., the highest point coordinates and the lowest point coordinates of the abdominal). In some embodiments, the radar echo signals may be desired to determine a physiological motion of the subject. One or more parameters (e.g., cardiac motion data or respiratory motion data) of the physiological motion may be used to control the scan of the medical device, which may reduce or avoid motion artifacts (e.g., motion artifacts caused by the cardiac motion or the breathing motion) in a reconstructed image. However, the radar echo signals may include disturbed signals caused by the rigid motion of the subject. The disturbed signals may be filtered in a subsequent processing operation. The use of the one or more radars 220 may be an effective physiological motion detection means instead of conventional means. For example, the conventional means may require one or more electrodes and/or respiratory zones attached to the body of the subject in order to detect the physiological motion of the subject, which may cause more or less discomfortable feeling for some subjects. By contrast, the use of the radar may reduce the discomfortable feeling, and ignore an installing time of the electrodes and/or respiratory zones, which may reduce the scan time of the medical device.

In some embodiment, the design of the one or more cameras 230 may aim at obtaining rigid motion information. A camera of the one or more cameras 230 may include a three-dimensional (3D) camera, such as a time of flight (TOF) camera, a structural light camera, a binocular camera, a LIDAR camera, or the like, or any combination thereof. The 3D camera may be configured to capture position and/or depth information of the subject. A 3D image or model of the subject may be reconstructed based on the captured position and/or depth information. It should be noted that light signals captured by the camera do not interfere with the radar echo signals captured by the radar. In some embodiments, the one or more cameras 230 may include various commercially available image capture devices for imaging. For example, the one or more cameras 230 may be configured to generate video images of the subject. The video images may include a sequence of image frames of the subject. The rigid motion may be identified by analyzing the sequence of image frames. In some embodiments, motion parameters regarding the rigid motion may be used to correct the radar echo data captured by the one or more radars 220. The corrected radar echo data may be used to generate accurate physiological information.

In some embodiments, the one or more cameras 230 may be disposed on various suitable positions for monitoring the rigid motion of the subject. For example, the one or more cameras 230 may be disposed on a component of the scanner 210, such as, on an RF receiving coil, in a cavity around the examination space, or on a scanning table. In some embodiments, the one or more cameras 230 and the one or more radars 220 may be disposed at the same position in the examination space of the scanner 210. In some embodiments, the one or more cameras 230 and the one or more radars 220 may be disposed at different positions, respectively. For example, the one or more radars 220 may be disposed in the cavity, and the one or more cameras 230 may be disposed on the RF receiving coil. In some embodiments, positions of the one or more cameras 230 and the one or more radars 220 may be adjusted according to the position of the subject, in order to detect corresponding signals from the subject within their coverage zone. The use of one or more cameras 230 is also a non-contactless detection for the subject, which may reduce the discomfortable feeling of the subject by contract with the contactless detection. In some embodiments, the one or more cameras 230 may be aligned at a certain angle towards the subject or at least a part of the subject, in order to obtain a larger detection angle and large-scale detection data.

In some embodiments, the radar and the camera may be integrated into a radar-camera sensor module (not shown in FIG. 2). The integrated radar-camera sensor module includes a radar component for transmitting radar signals and receiving reflected radar signals (i.e., radar echo signals) that are reflected from one or more objects within a coverage zone in a radar field. The integrated radar-camera sensor module may further include a camera component for capturing images based on light waves that are seen and captured within a coverage zone in a camera field. In some embodiments, the radar component and the camera component may be housed in a common housing. The common housing may be made of various materials, such as rigid materials, or non-rigid materials. In some embodiments, the radar component and the camera component may be coupled to processing circuits for processing the captured images and the received reflected radar signals, such as, fusing the captured images and the reflected radar signals. The fused data may be used to indicate vital signs of the subject, such as respiratory motion, heart motion.

In some embodiments, the camera component may include a plurality of optical elements and an imager. The camera component may include a commercially available image capture device for imaging. For example, the camera component may be configured to generate video images of the subject. The video images may include a plurality of image frames. In some embodiments, the radar component may include a radar transceiver coupled to an antenna. The transceiver and antenna operate to transmit radar signals within the desired coverage zone, and to receive radar echo signals reflected from the subject within the coverage zone. In some embodiments, the radar component may transmit a single fan-shaped radar beam and form multiple beams by receiving digital beamforming. In some embodiments, the antenna may include a vertical polarization antenna and/or a horizontal polarization antenna. The vertical polarization antenna may provide vertical polarization of the radar signals. The horizontal polarization antenna may provide horizontal polarization of the radar signals.

It should be noted that the above description of the medical device 200 is intended to be illustrative, and not to limit the scope of the present disclosure. For persons having ordinary skills in the art, multiple variations and modifications may be made under the teachings of the present disclosure. However, those variations and modifications do not depart from the scope of the present disclosure. For example, the one or more cameras 230 and the one or more radars 220 may be replaced by any other suitable device that is capable of collecting motion data of the subject.

Figure 3:
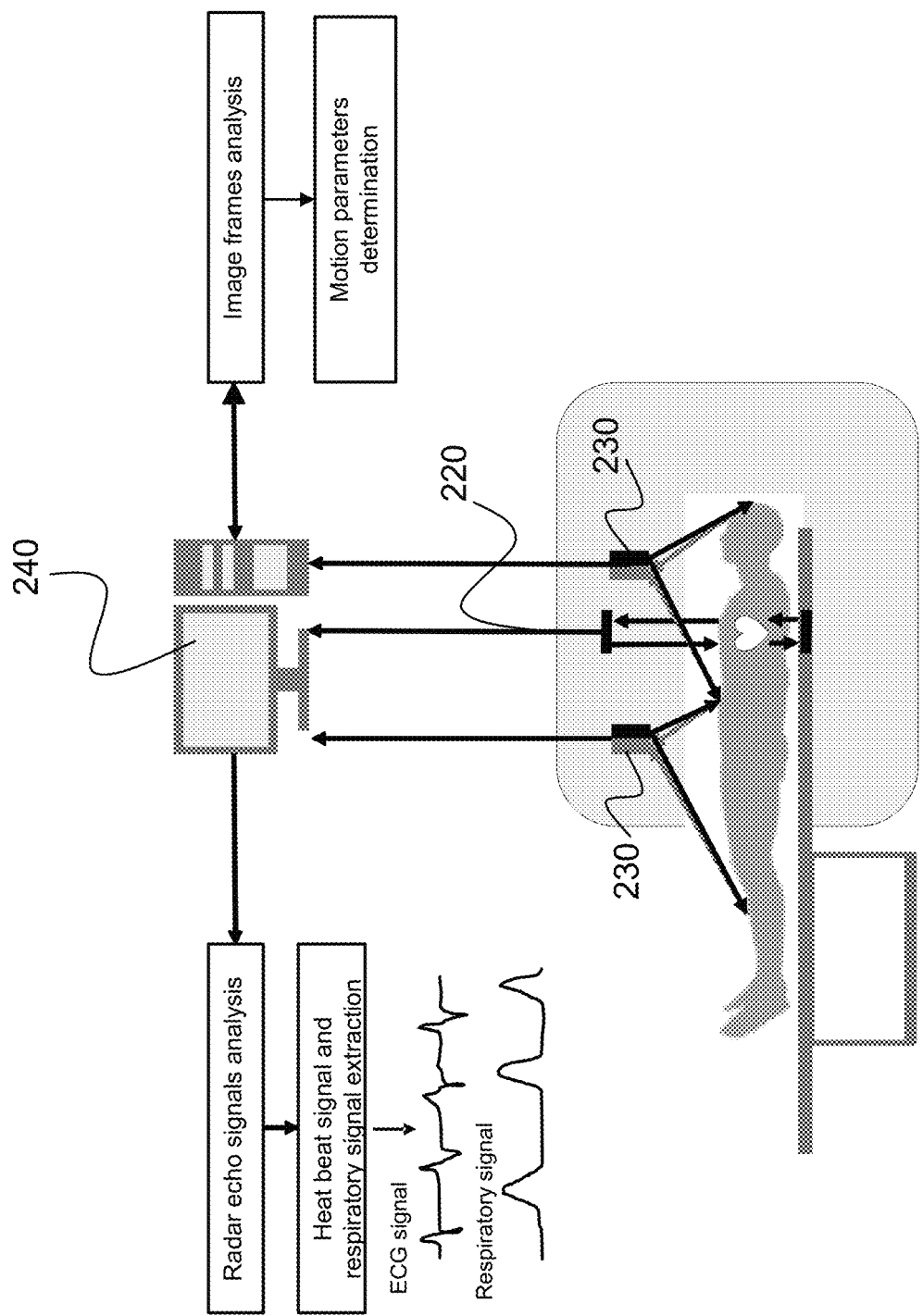
FIG. 3 is a schematic diagram illustrating an exemplary work scheme according to some embodiments of the present disclosure.

FIG. 3 is a schematic diagram illustrating an exemplary work scheme according to some embodiments of the present disclosure. As shown in FIG. 3, a radar 220 and two cameras 230 may be arranged in the examination space of the medical device. The radar 220 may be configured to acquire radar echo signals from the subject. The radar echo signals may provide information related to a physiological motion of the subject (e.g., respiratory motion, or heart motion). In some cases, the radar echo signals may include disturbed signals caused by a rigid motion of the subject (e.g., a head movement, a leg movement, a hand movement, etc.). The two cameras 230 may be configured to capture a plurality of image frames included the subject. The plurality of image frames may provide information related to the rigid motion of the subject. In some embodiments, the processing device 240 may perform one or more fusion operations for the plurality of image frames and the radar echo signals. For example, the one or more fusion operations may include image frames analysis and radar echo signals analysis. In some embodiments, the processing device 240 may perform the image frames analysis to determine one or more motion parameters regarding the rigid motion. The determined motion parameters may be transformed into a coordinate system corresponding to the radar 220. In some embodiments, the processing device 240 may perform the radar echo signals analysis to determine data related to the physiological motion, such as heart beat signal and/or respiratory signal as shown in FIG. 3. In some embodiments, the heart beat signal may be an electrocardiogram (ECG) signal. In some embodiments, the radar echo signal analysis may include one or more operations for correcting the radar echo signals based on the motion parameters regarding the rigid motion. For example, the processing device 240 may correct the radar echo signals by filtering out the disturbed signals caused by the rigid motion, and extract the heart beat signals (e.g., ECG signals) and the respiratory signals. In some embodiments, the extracted heat beat signals and/or respiratory signals may be used to control one or more scan operations of the medical device (e.g., the MRI device). In some embodiments, the processing device 240 may reconstruct a medical image (e.g., an MR image) based on the scan data acquired by the medical device (e.g., the MRI device). More descriptions about the image frames analysis and the radar echo signal analysis may be found elsewhere in the present disclosure (e.g., FIG. 7A and FIG. 8, and the descriptions thereof).

Figure 4:
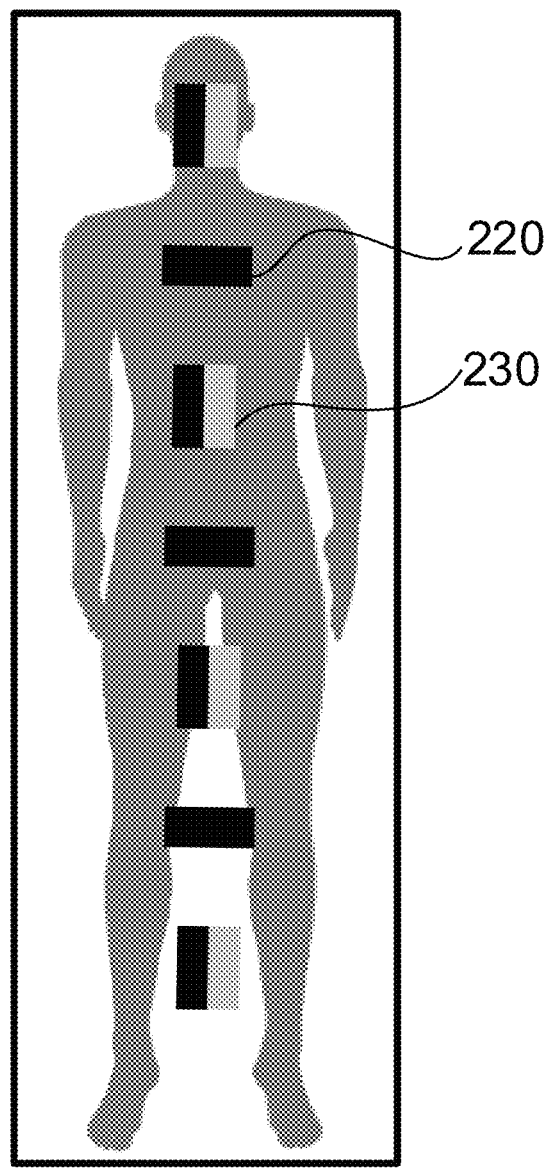
FIG. 4 is a schematic diagram illustrating an exemplary data acquisition according to some embodiments of the present disclosure.

FIG. 4 is a schematic diagram illustrating an exemplary data acquisition according to some embodiments of the present disclosure. In some embodiments, the one or more radars 220 and the one or more cameras 230 may acquire corresponding data simultaneously in response to a clock signal from a system clock of the medical device. In some embodiments, as illustrated in FIG. 4, the one or more radars 220 and the one or more cameras 230 may alternately capture corresponding data regarding various parts of the subject at different time points. In some embodiments, the detection angles of the one or more cameras 230 and the one or more radars 220 may be set according to a region of interest (ROI) of the subject. The ROI of the subject may be any part of the subject, such as, the head, the chest, a leg, and so on. For example, when the ROI is the chest region, the detection angle of the camera may be set as 60 degrees, and the detection angle of the radar may be set as 90 degrees. The one or more cameras 230 and the one or more radars 220 may acquire data within their own coverage zone. The acquired data may be used to characterize the motion of the subject (e.g., the physiological motion, or the rigid motion).

Figure 5:
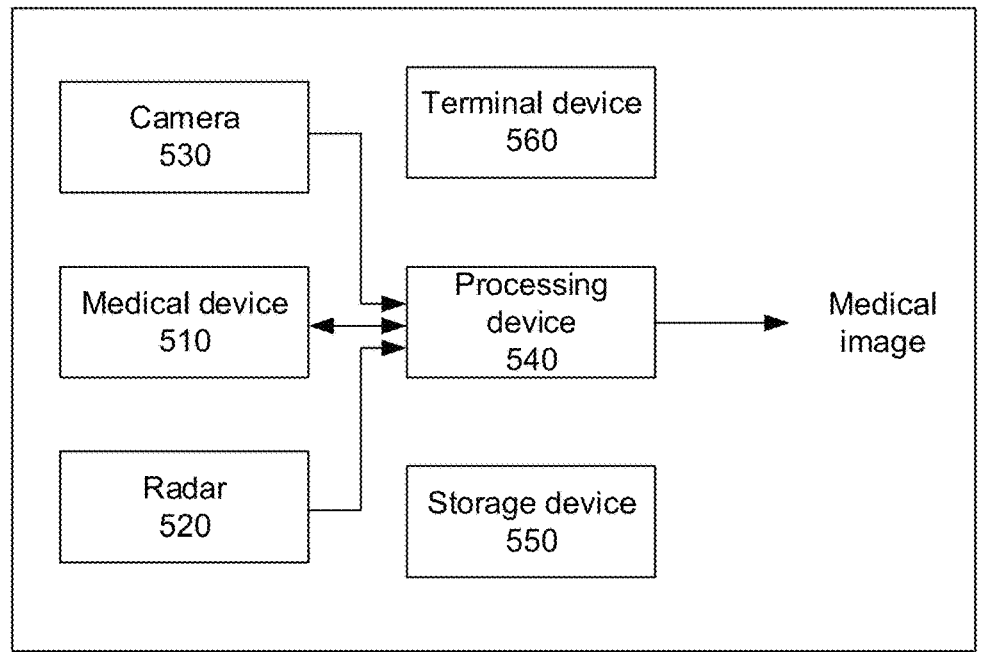
FIG. 5 is a block diagram illustrating an exemplary medical imaging system according to some embodiments of the present disclosure.

FIG. 5 is a block diagram illustrating an exemplary medical imaging system according to some embodiments of the present disclosure. As illustrated in FIG. 5, the medical imaging system 500 may include a medical device 510, a radar 520, a camera 530, a processing device 540, a storage device 550, and a terminal device 560. In some embodiments, the medical device 510 may scan a subject or at a part of the subject (e.g., an ROI of the subject). The radar 520 may acquire radar echo signals from the subject. The camera 530 may acquire a plurality of image frames including the subject. The processing device 540 may process the radar echo signals and the plurality of image frames to generate a control signal for controlling the medical device. In response to the control signal, the medical device 510 may obtain accurate scan data. The processing device 540 may reconstruct a medical image based on the scan data. In some embodiments, one or more components of the medical imaging system 500 (e.g., the camera 530, the radar 520, or the medical device 510) may be connected by various means. For example, the medical device 510, the radar 520, the camera 530, the terminal device 560, and/or the storage device 550 may be connected to the processing device 540 via a network (e.g., the network 150), or be connected to the processing device 540 directly.

In some embodiments, the medical device 510 may be used in medical treatments and/or diagnosis. The medical device 510 may be the same as or similar to the medical device 110 as illustrated in FIG. 1. Taking the IGRT device as an example, the IGRT device may irradiate a target (e.g., a lesion (or a tumor)) using various radioactive rays, such as, X-rays, y-rays, electron lines, proton beams, and so on. The IGRT device may include an accelerator (e.g., a linear accelerator or a cyclotron). The linear accelerator may generate and emit the radioactive rays (e.g., X-rays) to the target for killing cancer cells. A therapeutic effect on the tumor may be achieved. The accelerator may rotate with a gantry of the IGRT device in the clockwise or counterclockwise direction around an axis of the rack. The IGRT device may include a treatment table for supporting the subject. In some embodiments, the treatment table may be a six-dimensional platform capable of performing a linear motion in three directions of x, y, and z, and a rotational motion in three directions of x, y, and z. The treatment table may move the subject to a corresponding position (e.g., a target zone) accurately and/or quickly.

In some embodiments, the radar 520 may be the same as or similar to the radar 220. For example, the radar 520 may include a single-mode radar and/or a multi-mode radar. For example, the single-mode radar may include a continuous wave (CW) radar, a non-continuous wave radar (e.g., an ultra-wideband (UWB) radar, or a frequency modulated continuous wave (FMCW) radar), a light detection and ranging (LIDAR) device, and so on. The multi-mode radar may include a CW-UWB radar, a CW-FMCW radar, or a UWB-FMCW radar, and so on. In some embodiments, the camera 530 may be the same as or similar to the camera 230. For example, the camera may include a three-dimensional (3D) camera, such as a time of flight (TOF) camera, a structured light camera, a binocular camera, a LIDAR camera, or the like, or any combination thereof. More descriptions of the radar and the camera may be found elsewhere in the present disclosure. See, e.g., FIG. 2, and the descriptions thereof.

In some embodiments, the processing device 540 may process data and/or information obtained from the medical device 510, the terminal device 560, the storage device 550, the camera 530, and/or the radar 520. For example, the processing device 540 may determine first data regarding a first motion of the subject. The first motion may include a rigid motion of the subject. The first data may be rigid motion related data, such as, motion parameters. As another example, the processing device 540 may determine second data regarding a second motion of the subject. The second motion may include a physiological motion of the subject. The second data may be physiological motion related data, such as cardiac motion data or respiratory motion data. As a further example, the processing device 540 may generate a control signal for controlling the device based on the first data and the second data. In some embodiments, the processing device 540 may be the same as or similar to the processing device 120 illustrated in FIG. 1. For example, the processing device 540 may be a single server or a server group. As another example, the processing device 540 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the storage device 550 may store data and/or instructions. In some embodiments, the storage device 550 may store data obtained from medical device 510, the radar 520, the camera 530, the processing device 540, and the terminal device 560. In some embodiments, the storage device 550 may store data and/or instructions that the processing device 540 may execute or use to perform exemplary methods described in the present disclosure. The storage device 550 may be the same as or similar to the storage device 130 illustrated in FIG. 1. For example, the storage device 550 may include a mass storage device, a removable storage device, a volatile read-and-write memory, a read-only memory (ROM), or the like, or any combination thereof.

In some embodiments, the terminal device 560 may be connected to and/or communicate with the medical device 510, the radar 520, the camera 530, the processing device 540, and/or the storage device 550. For example, the terminal device 560 may obtain a processed image from the processing device 540. As another example, the terminal device 560 may obtain scan data acquired by the medical device 510 and transmit the scan data to the processing device 540 to be processed. In some embodiments, the terminal device 560 may be the same as or similar to the terminal(s) 140 illustrated in FIG. 1. For example, the terminal device 560 may include a mobile device, a tablet computer, a laptop computer, or the like, or any combination thereof.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 550 may be a data storage including cloud computing platforms, such as, a public cloud, a private cloud, a community cloud, and a hybrid cloud, etc. However, those variations and modifications do not depart from the scope of the present disclosure.

Figure 6:
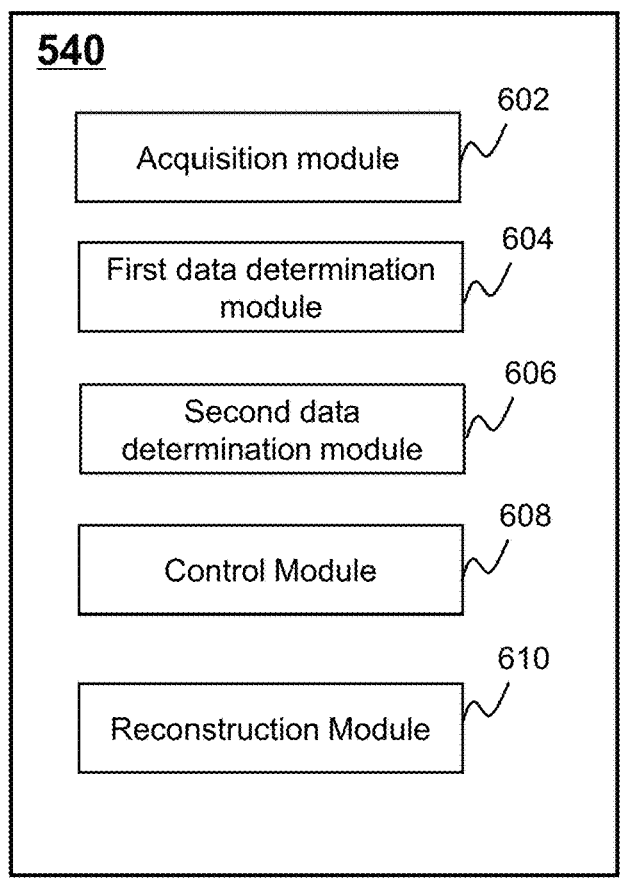
FIG. 6 is a block diagram illustrating an exemplary processing device according to some embodiments of the present disclosure.

FIG. 6 is a block diagram illustrating an exemplary processing device according to some embodiments of the present disclosure. In some embodiments, the processing device 540 may be in communication with a computer-readable storage medium (e.g., the storage device 550 illustrated in FIG. 5, the storage device 130 illustrated in FIG. 1) and may execute instructions stored in the computer-readable storage medium. The processing device 540 may include an acquisition module 602, a first data determination module 604, a second data determination module 606, a control module 608, and a reconstruction module 610.

The acquisition module 602 may be configured to acquire data from one or more modules of the processing device 540. In some embodiments, the acquisition module 602 may obtain first data regarding a first motion of a subject in an examination space of a medical device. In some embodiments, the first data determination module 604 may determine the first data regarding the first motion. The acquisition module 602 may obtain the first data from the first data determination module 604. In some embodiments, the acquisition module 602 may acquire a plurality of image frames of the subject through one or more cameras. The one or more cameras may be installed on the medical device. The plurality of image frames may be used to determine the first data. In some embodiments, the acquisition module 602 may obtain second data regarding a second motion of the subject. In some embodiments, the second data determination module 606 may determine the second data regarding the second motion of the subject. The acquisition module 602 may obtain the second data from the second data determination module 606. In some embodiments, the acquisition module 602 may acquire radar echo data through one or more radars. The one or more radars may be installed on the medical device. The radar echo data may be used to determine the second data. In some embodiments, the first motion may include a rigid motion, and the second motion may include a physiological motion.

The first data determination module 604 may determine, based on at least a part of the plurality of image frames, first data including one or more motion parameters. For example, the first data determination module 604 may process the plurality of image frames to identify the rigid motion of the subject. For example, the first data determination module 604 may determine one or more motion parameters of the first motion based on at least a part of the plurality of image frames. In some embodiments, the one or more motion parameters may include a three-dimensional translation matrix and/or a three-dimensional rotation matrix. In some embodiments, the first data determination module 604 may determine the one or more motion parameters using an image registration technique. Exemplary image registration techniques may include but not be limited to a pixel-based registration algorithm, a feature-based registration algorithm, a contour-based registration algorithm, a mutual information-based registration algorithm, and so on. More descriptions of the determination of the first data may be found elsewhere in the present disclosure (e.g., FIG. 8 and the description thereof).

The second data determination module 606 may determine the second data regarding the second motion of the subject. In some embodiments, the second motion may include a physiological motion of the subject. The physiological motion may include a heart motion and/or respiratory motion of the subject. In some embodiments, the second data determination module 606 may process the radar echo data to identify the physiological motion of the subject. For example, the second data determination module 606 may correct the acquired radar echo data by filtering out disturbed information caused by the rigid motion. The second data determination module 606 may extract the second data from the corrected radar echo data. The second data may include cardiac motion data or respiratory motion data. More descriptions of the determination of the second data may be found elsewhere in the present disclosure (e.g., FIG. 8 and the description thereof).

The control module 608 may generate, based on the first data and the second data, a control signal for controlling the medical device to scan at least a part of the subject. More specifically, the control module 608 may generate the control signal based on the cardiac motion data and/or the respiratory motion data. The cardiac motion data and/or the respiratory motion data may be determined based on the first data and the second data. In some embodiments, the control module 608 may generate the control signal using a gating technique. The gating technique may include a cardiac gating and a respiratory gating. In response to the control signal, the medical device may be directed to scan the subject or at least a part of the subject.

The reconstruction module 610 may reconstruct a medical image based on the scan data acquired by the medical device. For example, the reconstruction module 610 may reconstruct the image using one or more reconstruction algorithms. The one or more reconstruction algorithms may include but not limited to a 2-dimensional Fourier transform technique, a back projection technique (e.g., a convolution back projection technique, a filtered back projection technique), an iteration reconstruction technique, etc. Examples of iterative reconstruction techniques may include a simultaneous algebraic reconstruction technique (SART), a simultaneous iterative reconstruction technique (SIRT), an ordered subset convex technique (OSC), ordered subset maximum likelihood methodologies, an ordered subset expectation maximization (OSEM) methodology, an adaptive statistical iterative reconstruction technique (ASIR) methodology, a least squares QR methodology, an expectation maximization (EM) methodology, an OS-separable paraboloidal surrogates technique (OS-SPS), an algebraic reconstruction technique (ART), a Kacsmarz reconstruction technique, or any other iterative reconstruction technique or methodology that meets application-specific requirements.

It should be noted that the descriptions above in relation to processing device 540 are provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. In some embodiments, the processing device 540 may include one or more other modules. For example, the processing device 540 may include a storage module to store data generated by the modules in the processing device 540. In some embodiments, any two of the modules may be combined as a single module, and any one of the modules may be divided into two or more units.

Figure 7A:
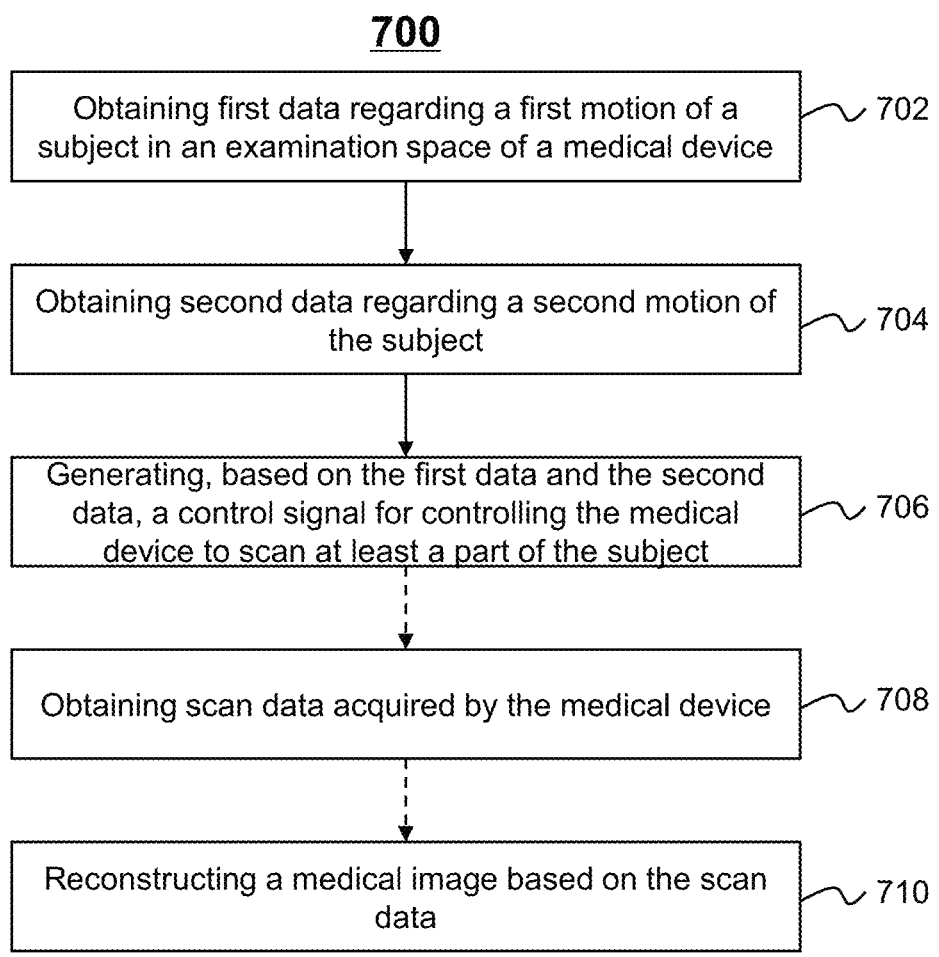
FIG. 7A is a flowchart illustrating an exemplary process for controlling a medical device according to some embodiments of the present disclosure.

FIG. 7A is a flowchart illustrating an exemplary process for controlling a medical device according to some embodiments of the present disclosure. Process 700 may be implemented in the medical system 100 illustrated in FIG. 1 or the medical imaging system 500 illustrated in FIG. 5. For example, the process 700 may be stored in the storage device 130 and/or the storage device 550 in the form of instructions (e.g., an application), and invoked and/or executed by the processing device 120 (e.g., the processing device 540 illustrated in FIG. 5, or one or more modules in the processing device 540 illustrated in FIG. 6). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 702, the processing device (e.g., the acquisition module 602 of the processing device 540) may obtain first data regarding a first motion of a subject in an examination space of a medical device. In some embodiments, the first data determination module 604 of the processing device 540 may determine the first data regarding the first motion of the subject in the examination space of the medical device. The acquisition module 602 may obtain the first data from the first data determination module 604. In some embodiments, the first motion may refer to a rigid motion. The rigid motion may include a translational and/or rotational motion of the subject. Exemplary rigid motions may include a pose motion of the subject, such as the rotating or nodding of the head of the subject, a motion of a leg, a motion of a hand, and so on. The first data may refer to data related to the first motion (e.g., the rigid motion). Hereinafter the first data may be referred to as first motion related data, rigid motion related data, or pose motion related data.

In some embodiments, the acquisition module 602 may acquire, via one or more cameras (e.g., the one or more cameras 230, or the camera 530), a plurality of image frames regarding the first motion of the subject in the examination space of the medical device. The one or more cameras may capture the plurality of image frames including the subject. The plurality of image frames may be sent to the acquisition module 602. The first data determination module 604 may process the plurality of image frames to identify the rigid motion of the subject. For example, the first data determination module 604 may determine one or more motion parameters of the first motion based on at least a part of the plurality of image frames. In some embodiments, the one or more motion parameters may include a three-dimensional translation matrix and/or a three-dimensional rotation matrix. In some embodiments, the first data determination module 604 may determine the one or more motion parameters using an image registration technique. Exemplary image registration techniques may include a pixel-based registration algorithm, a feature-based registration algorithm, a contour-based registration algorithm, a mutual information-based registration algorithm, and so on. More descriptions of the determination of the first data may be found elsewhere in the present disclosure (e.g., FIG. 8 and the description thereof).

In 704, the processing device (e.g., the acquisition module 602 of the processing device 540) may obtain second data regarding a second motion of the subject. In some embodiments, the second data determination module 606 of the processing device 540 may determine the second data regarding the second motion of the subject. The acquisition module 602 may obtain the second data from the second data determination module 606. In some embodiments, the second motion may include a physiological motion of the subject. The physiological motion may include a cardiac motion, a respiratory motion, or the like, of the subject. The second data may refer to data related to the second motion (e.g., the physiological motion). Hereinafter the second data may be referred to as second motion related data, or physiological motion related data.

In some embodiments, the acquisition module 602 may acquire, via one or more radars (e.g., the one or more radars 220, or the radar 520), radar echo data from the subject. For example, the one or more radars may emit radar signals to the subject or at least a part of the subject, and receive the radar echo signals reflected from the subject. The radar echo signals may include motion information of the subject. The motion information may include not only the physiological motion information, but also the rigid motion information.

In this case, the radar echo signals caused by the rigid motion may be designated as disturbed signals. The acquired radar echo data may be sent to the acquisition module 602. The second data determination module 606 may process the radar echo data to identify the physiological motion of the subject. For example, the second data determination module 606 may correct the acquired radar echo data by filtering out the disturbed information caused by the rigid motion. The second data determination module 606 may extract the second data from the corrected radar echo data. The second data may include cardiac motion data or respiratory motion data. In some embodiments, the second data relating to the physiological motion of the subject determined from the radar echo data acquired by the radar(s) may also be referred to as second physiological motion data or sensor-based physiological motion data in the present disclosure. More descriptions of the determination of the second data may be found elsewhere in the present disclosure (e.g., FIG. 8 and the description thereof).

In 706, the processing device (e.g., a control module 608 of the processing device 540) may generate, based on the first data and the second data, a control signal for controlling the medical device to scan at least a part of the subject. In some embodiments, the processing device 540 may generate accurate cardiac motion data and/or respiratory motion data based on the first data and the second data. The accurate cardiac motion data and respiratory motion data may reduce or avoid motion artifacts (e.g., cardiac motion artifacts or respiratory motion artifacts) in a reconstructed image. For example, the second data determination module 606 may correct the radar echo data according to the one or more motion parameters of the first motion. The disturbed component of the radar echo data may be removed by the correction. The cardiac motion data and/or the respiratory motion data extracted from the corrected radar echo data may be more accurate than the uncorrected radar echo data. In some embodiments, the control module 608 may generate the control signal using a gating technique. The gating technique may be used for synchronization of signal (e.g., an MR signal) acquisition to the cardiac and/or respiratory cycle.

Figure 7B:
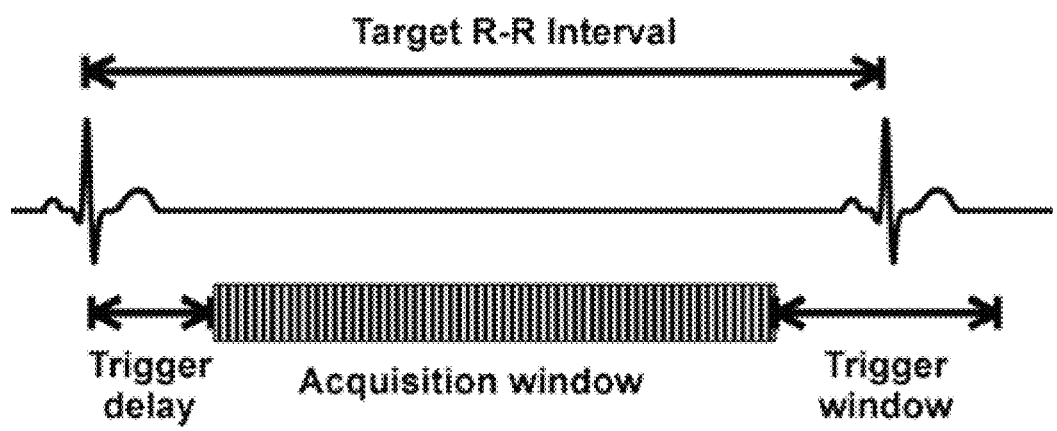
FIG. 7B is a schematic diagram illustrating an exemplary cardiac gating according to some embodiments of the present disclosure.

In some embodiments, the gating technique may include a cardiac gating and/or a respiratory gating. For example, the cardiac gating may be based on cardiac motion data (e.g., an ECG signal). The ECG signal may show a plurality of cardiac cycles. Each cardiac cycle may correspond to a heartbeat. In some embodiments, one cardiac cycle may be a time interval between two R-waves of the ECG signal. Merely by way of example, FIG. 7B illustrates an exemplary cardiac gating according to some embodiments of the present disclosure. As illustrated in FIG. 7B, in a specific time point between two R-waves (e.g., an end of a trigger delay, or a beginning of an acquisition window), the control module 608 may generate a control signal (e.g., a gating signal) for triggering the medical device (e.g., the MRI device) to scan in order to acquire scan data. The trigger delay may be defined as the time interval between the first R-wave and the beginning of data acquisition. The scan data may be acquired during the acquisition window. The control module 608 may generate the control signal for each scan based on the ECG signal. The use of the cardiac gating technique may facilitate to reduce or avoid the cardiac motion artifacts.

Figure 7C:
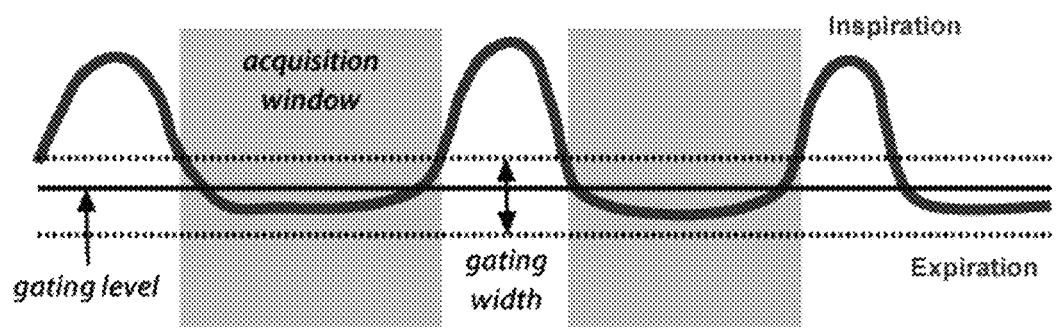
FIG. 7C is a schematic diagram illustrating an exemplary respiratory gating according to some embodiments of the present disclosure.

As another example, FIG. 7C illustrates an exemplary respiratory gating according to some embodiments of the present disclosure. The respiratory gating may be based on respiratory data. The respiratory data may show a plurality of respiratory cycles as shown in FIG. 7C. The respiratory cycle may be a cycle of inspiration and expiration. The acquisition window may be defined as a time interval when an amplitude of the respiratory signal is within the gating width. The scan data may be acquired during the acquisition window. In some embodiments, when the amplitude of the respiratory signal is within the gating width, the control module 608 may generate a control signal (e.g., a gating signal) for triggering the medical device (e.g., the MRI device) to scan and acquiring scan data during expiration (when least diaphragmatic movement occurs).

In some embodiments, the gating technique may be used to control various medical devices for reducing motion artifacts. For example, an ECG-gated technique may be used to perform a CT scan (e.g., for cardiac imaging). As another example, the respiratory and cardiac gating technique may be used to perform a PET scan (e.g., for cardiac PET imaging). As a further example, the respiratory gating may be used to monitor the movement of a tumor during normal breathing of a subject in a radiotherapy session. When the tumor moves outside a target field, a gating signal for turning off the treatment beam may be generated according to the respiratory gating.

In 708, the processing device (e.g., the acquisition module 602 of the processing device 540) may obtain scan data acquired by the medical device. For example, in response to the control signal, the medical device may be directed to scan the subject or at least part of the subject. In some embodiments, the scan data may be stored in the storage device 130. The acquisition module 602 may send the scan data to the reconstruction module 610 for further processing.

In 710, the processing device (e.g., the reconstruction module 610 of the processing device 540) may reconstruct a medical image based on the scan data. In some embodiments, the reconstruction module 610 may reconstruct the image using one or more reconstruction algorithms. For example, the one or more reconstruction algorithms may include a 2-dimensional Fourier transform technique, a back projection technique (e.g., a convolution back projection technique, a filtered back projection technique), an iteration reconstruction technique, etc. Examples of iterative reconstruction techniques may include a simultaneous algebraic reconstruction technique (SART), a simultaneous iterative reconstruction technique (SIRT), an ordered subset convex technique (OSC), ordered subset maximum likelihood methodologies, an ordered subset expectation maximization (OSEM) methodology, an adaptive statistical iterative reconstruction technique (ASIR) methodology, a least squares QR methodology, an expectation maximization (EM) methodology, an OS-separable paraboloidal surrogates technique (OS-SPS), an algebraic reconstruction technique (ART), a Kacsmarz reconstruction technique, or any other iterative reconstruction technique or methodology that meets application-specific requirements.

It should be noted that the description of the process 700 is provided for the purposes of illustration, and not intended to limit the scope of the present disclosure. For persons having ordinary skills in the art, various variations and modifications may be conducted under the teaching of the present disclosure. For example, operations 702 and 704 may be integrated into a single operation. As another example, operations 704 and 706 may be integrated into a single operation. However, those variations and modifications may not depart from the protection of the present disclosure.

Figure 8:
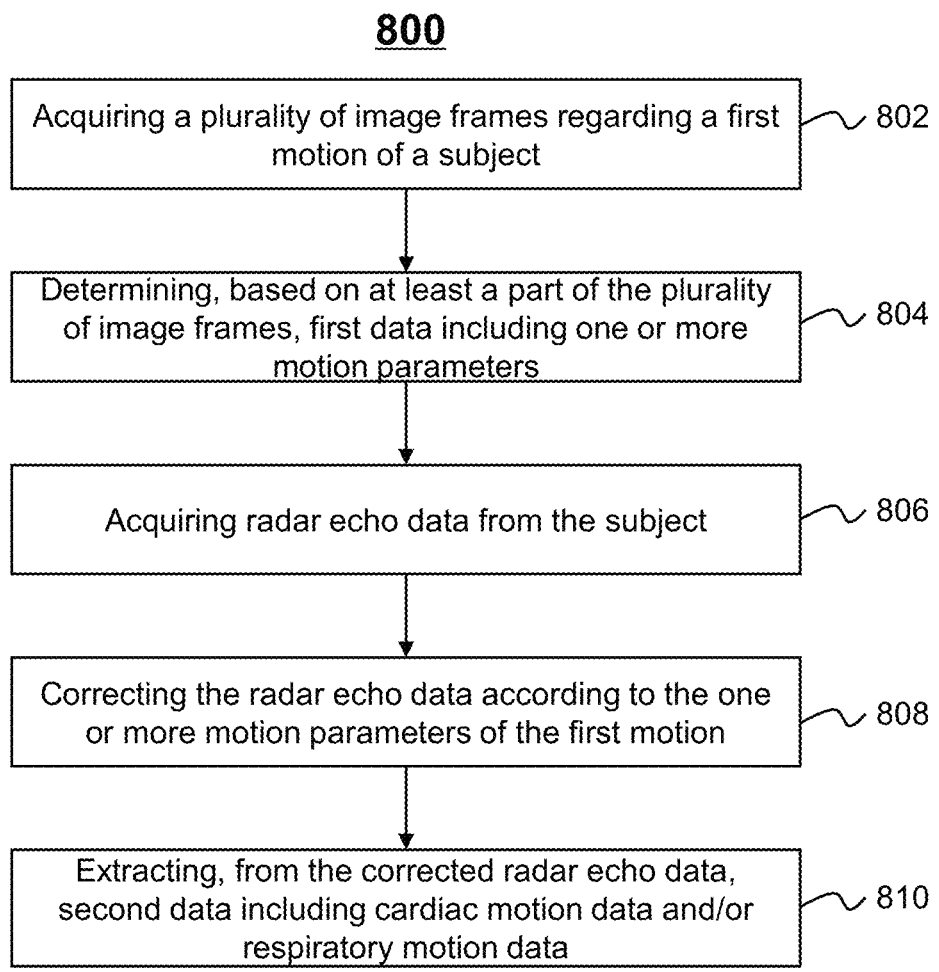
FIG. 8 is a flowchart illustrating an exemplary process for extracting physiological motion related data according to some embodiments of the present disclosure.

FIG. 8 is a flowchart illustrating an exemplary process for extracting physiological motion related data according to some embodiments of the present disclosure. Process 800 may be implemented in the medical system 100 illustrated in FIG. 1 or the medical imaging system 500 illustrated in FIG. 5. For example, the process 800 may be stored in the storage device 130 and/or the storage device 550 in the form of instructions (e.g., an application), and invoked and/or executed by the processing device 120 (e.g., the processing device 540 illustrated in FIG. 5, or one or more modules in the processing device 540 illustrated in FIG. 6). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 802, the processing device (e.g., the acquisition module 602 of the processing device 540) may acquire a plurality of image frames regarding a first motion of a subject.

In some embodiments, the first motion may refer to a rigid motion. The rigid motion may include a translational and/or rotational motion of the subject. Exemplary rigid motions may include a pose motion of the subject, such as the rotating or nodding of the head of the subject, leg motion, hand motion, and so on. The rigid motion may be identified by a sequence of image frames. In some embodiments, one or more cameras (or other image capture devices) installed on the medical device (e.g., the medical device 110 or the medical device 510) may capture the sequence of image frames of the subject. The one or more cameras may be installed on suitable positions of the medical device in order to capture the sequence of image frames of the subject. In some embodiments, the captured image frames may be stored in a storage device (e.g., the storage device 130 or the storage device 550). The acquisition module 602 may acquire the image frames from the storage device.

In 804, the processing device (e.g., the first data determination module 604 of the processing device 540) may determine, based on at least a part of the plurality of image frames, first data including one or more motion parameters.

In some embodiments, the first data may refer to data related to the first motion (e.g., the rigid motion). In some embodiments, the first data determination module 604 may determine the one or more motion parameters according to the at least a part of the plurality of image frames. The one or more motion parameters may include a three-dimensional translation matrix and/or a three-dimensional rotation matrix. The rigid motion (i.e., the first motion) may be measured by the one or more motion parameters.

In some embodiments, the one or more motion parameters may be determined using a tracking marker. Specifically, the tracking marker may be fixed on the subject or an ROI of the subject during the scan of the medical device. The tracking marker may be represented as a specific image texture in an image frame. In some embodiments, the rigid motion of the subject may be identified by tracking the motion of the tracking marker in at least two of the plurality of image frames. The first data determination module 604 may segment the tracking marker and the subject (or the ROI of the subject) from the image frame. The first data determination module 604 may obtain coordinates of the tracking marker in different image frames, respectively. The obtained coordinates are the coordinates in the camera coordinate system (hereinafter camera coordinates related to the tracking marker). The first data determination module 604 may determine the motion parameters based on the camera coordinates related to the tracking marker in different image frames.

Assuming that $f_0$ denotes a first image frame captured at the time point $t_0$, $f_1$ denotes a second image frame captured at the time point $t_1$. $X_{c0}$ denotes the coordinates related to the tracking marker at $t_0$, and $X_{c1}$ denotes the coordinates related to the tracking marker at $t_1$. Let $R_c$ be a rotation matrix and $T_c$ be a translation matrix for the rigid motion of the tracking marker between $t_0$ and $t_1$, respectively. The rigid motion may be described by Equation (1) as follows:

$$X_{c1}=R_c X_{c0}+T_c. \quad (1)$$

In some embodiments, $X_{c0}$ and $X_{c1}$ may be a 3×N dimensional matrix, where N denotes the number (or count) of the tracking marker(s). In some embodiments, Equation (2) may be introduced to determine $R_c$ and $T_c$:

$$C=[X_{c0}-\overline{X_{c0}}][X_{c1}-\overline{X_{c1}}], \quad (2)$$

where $\overline{X_{c0}}$ and $\overline{X_{c1}}$ are mean coordinate matrices of N tracking markers, respectively. In some embodiments, the first data determination module 604 may solve Equation (2) using, e.g., singular value decomposition (SVD). $R_c$ and $T_c$ may be determined based on the solutions of Equation (2). In some embodiments, if $R_c$ and $T_c$ are zero matrices, then no rigid motion exists between the time points $t_0$ and $t_1$. In other words, the subject did not move between the time points $t_0$ and $t_1$. In some embodiments, if at least one of $R_c$ and $T_c$ is a non-zero matrix, there may exist rigid motion between the time points $t_0$ and $t_1$. In other words, the subject may have moved between the time points $t_0$ and $t_1$. The rigid motion may be identified based on the motion parameters. In some embodiments, the rigid motion related data (e.g., the motion parameters) may be fed back to the one or more radars.

In 806, the processing device (e.g., the acquisition module 602 of the processing device 540) may acquire radar echo data from the subject. In some embodiments, the radar echo data and the plurality of image frames may be acquired simultaneously by the one or more radars and the one or more cameras, respectively. That is, operation 802 and operation 806 may be performed simultaneously.

In some embodiments, the acquisition module 602 may acquire the radar echo data acquired by the one or more radars in real time. Exemplary radars may include a continuous wave (CW) radar, an ultra-wideband (UWB) radar, or a frequency modulated continuous wave (FMCW) radar, and so on. The one or more radars may be installed at suitable positions on or in the vicinity of the medical device in order to capture radar echo signals indicative of the physiological motion (i.e., the second motion) of the subject. In some embodiments, the captured radar echo data may be stored in a storage device (e.g., the storage device 130 or the storage device 550). The acquisition module 602 may acquire the radar echo data from the storage device 130. In some embodiments, the one or more radars may detect both the physiological motion and the rigid motion if there exists the rigid motion during the scan. In this case, if the radar echo data without a correction is used to determine physiological motion related data directly, the determined physiological motion related data may be inaccurate because the radar echo data includes disturbed information caused by the rigid motion.

In 808, the processing device (e.g., the second data determination module 606 of the processing device) may correct the radar echo data according to the one or more motion parameters of the first motion (e.g., the rigid motion).

The determined one or more motion parameters, based on Equation (1) and Equation (2), correspond to the camera coordinate system. To correct the radar echo data, the one or more motion parameters in the camera coordinate system may be transformed into the radar coordinate system. In some embodiments, system calibration between the camera coordinate system and the radar coordinate system may be performed.

Figure 9:
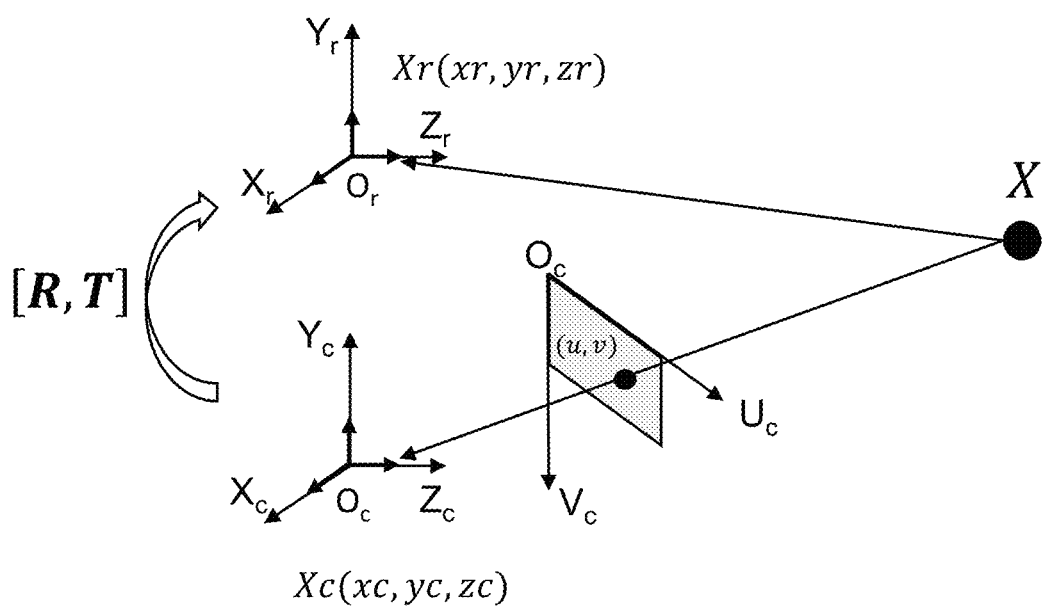
FIG. 9 is a schematic diagram illustrating an exemplary system calibrating according to some embodiments of the present disclosure.

Merely by way of example, FIG. 9 illustrates an exemplary system calibration between the camera coordinate system and the radar coordinate systems according to some embodiments of the present disclosure. As shown in FIG. 9, let $O_c X_c Y_c Z_c$ be the camera coordinate system, and let $O_r X_r Y_r Z_r$ be the radar coordinate system. The system calibration may be described by Equation (3) as follows:

$$X_r=R_{cr}X_c+T_{cr}, \quad (3)$$

where $X_r$ denotes the coordinates in the radar coordinate system, $X_c$ denotes the coordinates in the camera coordinate system, $R_{cr}$ denotes the rotation matrix between the camera coordinate system and the radar coordinate system, and $T_{cr}$ denotes the translation matrix between the camera coordinate system and the radar coordinate system. In some embodiments, the second data determination module 606 may determine one or more motion parameters corresponding to the radar coordinates system (also referred to as second motion parameters) based on the one or more motion parameters corresponding to the camera coordinate system (also referred to as first motion parameters). The second motion parameters may include the rotation matrix $R_r$ and the translation matrix $T_r$ in the radar coordinate system. In some embodiments, because the second motion parameters and the radar echo data are in the same coordinate system, the second data determination module 606 may correct the radar echo data based on the second motion parameters. For example, the second data determined module 606 may determine disturbed information corresponding to the second motion parameters, and correct the radar echo data by filtering out the disturbed information.

Assuming that $X_{r0}$ denotes the coordinates of a tracking marker in the radar coordinate system at $t_0$, and $X_{r1}$ denotes the coordinates of the tracking marker in the radar coordinate system at $t_1$. Thus, $$X_{r0}=R_{cr}X_{c0}+T_{cr}, \quad (4)\text{ and}$$

$$X_{r1}=R_{cr}X_{c1}+T_{cr}. \quad (5)$$

In some embodiments, $X_{r1}$ may be described by combining Equation (1) and Equation (4):

$$X_{r1}=R_{cr}R_c R_{cr}^{-1}X_{r0}-R_{cr}R_c R_{cr}^{-1}T_{cr}+R_{cr}T_c+T_{cr}=R_r X_{r0}+T_r. \quad (6)$$

In some embodiments, the second data determination module 606 may determine the rotation matrix $R_r$ and the translation matrix $T_r$ in the radar coordinate system based on Equation (6). For example, $$R_r=R_{cr}R_c R_{cr}^{-1}, \text{ and } T_r=-R_{cr}R_c R_{cr}^{-1}T_{cr}+R_{cr}T_c+T_{cr}. \quad (7)$$

In 810, the processing device (e.g., the second data determination module 606 of the processing device) may extract, from the corrected radar echo data, the second data including cardiac motion data and/or respiratory motion data.

In some embodiments, the second data may refer to data related to the second motion (e.g., the physiological motion).

The second data may include cardiac motion data (e.g., an ECG signal) and respiratory motion data. Specifically, the second data determination module 606 may extract, from the corrected radar echo data, the cardiac motion data, and the respiratory motion data, respectively. For example, the second data determination module 606 may perform an oblique removal operation for the corrected radar echo data. The oblique removal operation may include: it mixes an input signal with a reference signal (a local oscillator signal with appropriate delay, the delay is usually estimated from the result of narrowband signal ranging); then each scattering point corresponds to a single frequency component after mixing, and a discrete Fourier transformation (DFT) is performed for the mixed-frequency output signal. The second data determination module 606 may filter the radar echo data after the oblique removal. The filtered radar echo data may be amplified by an amplifier. The amplified radar echo data may be divided into the cardiac motion data and respiratory motion data by a signal separator (e.g., a demultiplexer). In some embodiments, the cardiac motion data and the respiratory motion data may be sent to the medical device for real time controlling the medical device.

Figure 10:
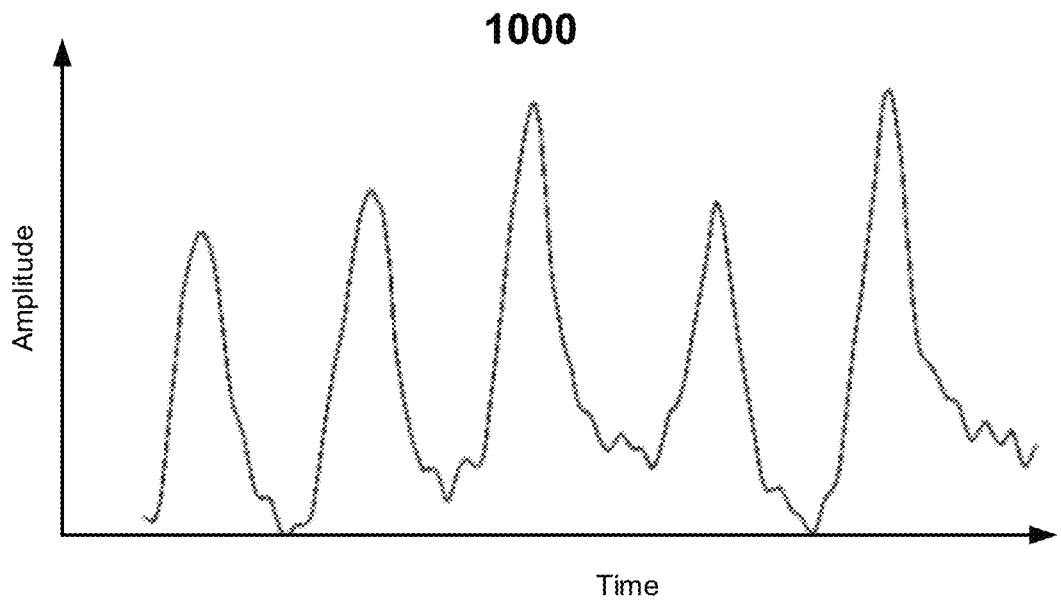
FIG. 10 is a schematic diagram illustrating an exemplary respiratory signal according to some embodiments of the present disclosure.
Figure 11:
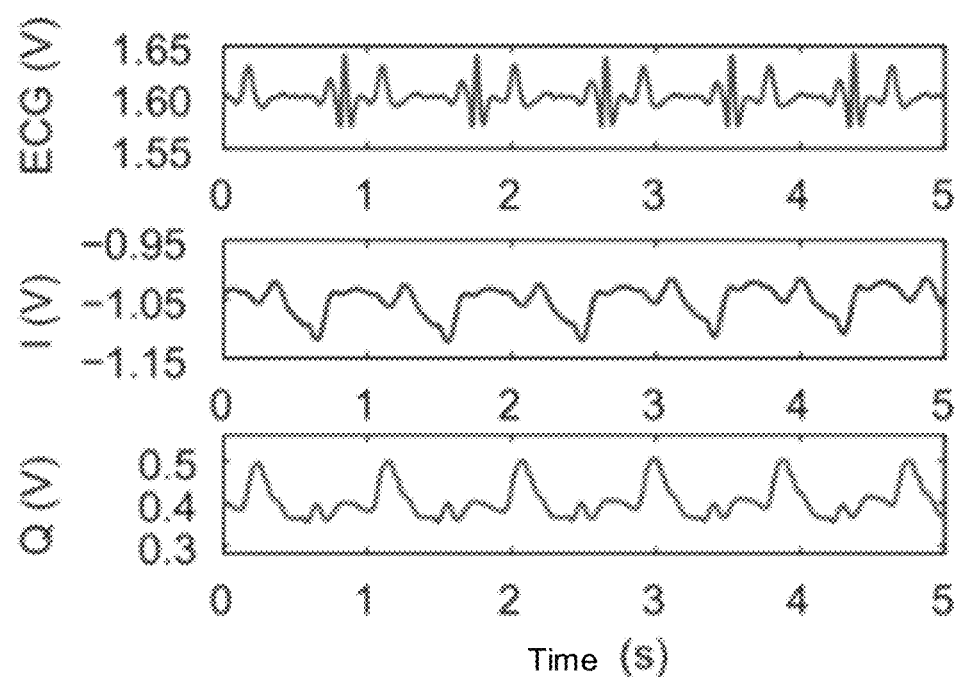
FIG. 11 is a schematic diagram illustrating an exemplary ECG signal according to some embodiments of the present disclosure.

Merely by way of example, FIG. 10 illustrates an exemplary respiratory signal 1000, and FIG. 11 illustrates an exemplary ECG signal. FIG. 10 shows a respiratory signal 1000 extracted from the radar echo signal after the rigid motion correction. The respiratory signal may include a respiratory waveform. The respiratory waveform may include a plurality of respiratory cycles. FIG. 11 shows an ECG signal extracted from the radar echo data after the rigid motion correction. The ECG signal may be extracted based on the Q channel and I channel of the radar echo signal. Q channel and I channel are two orthogonal channels of the radar.

Figure 12:
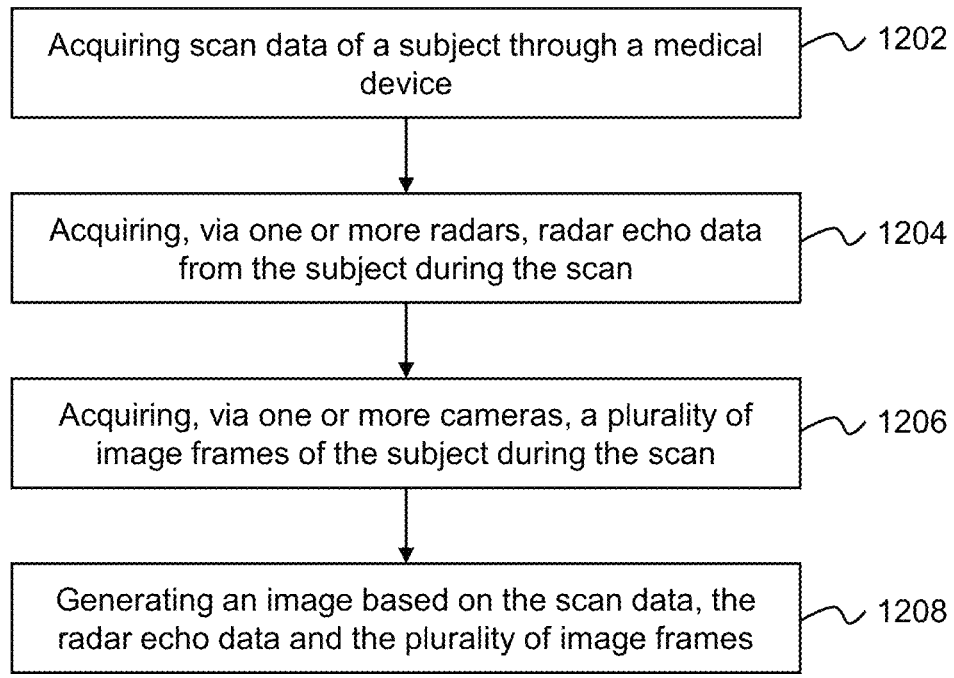
FIG. 12 is a flowchart illustrating an exemplary process for generating an image according to some embodiments of the present disclosure.

FIG. 12 is a flowchart illustrating an exemplary process for generating an image according to some embodiments of the present disclosure. Process 1200 may be implemented in the medical system 100 illustrated in FIG. 1 or the medical imaging system 500 illustrated in FIG. 5. For example, the process 1200 may be stored in the storage device 130 and/or the storage device 550 in the form of instructions (e.g., an application), and invoked and/or executed by the processing device 120 (e.g., the processing device 540 illustrated in FIG. 5, or one or more modules in the processing device 540 illustrated in FIG. 6). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1202, the processing device (e.g., the acquisition module 602 of the processing device 540) may acquire scan data of a subject through a medical device. For example, during the medical device (e.g., an MRI device) scans the subject or at least a part of the subject, the acquisition module 602 may acquire the scan data related to the subject or the at least a part of the subject in real time or near real time. The acquired scan data may be stored in a storage device (e.g., the storage device 550).

In 1204, the processing device (e.g., the acquisition module 602 of the processing device 540) may acquire, via one or more radars, radar echo data from the subject during the scan. The radar echo data may be used to characterize a physiological motion (i.e., the second motion mentioned above) of the subject. In some embodiments, the one or more radars may be installed at suitable positions on or in the vicinity of the medical device in order to capture radar echo signals indicative of the physiological motion of the subject. In some embodiments, the radar echo data may be stored in a storage device (e.g., the storage device 550).

In 1206, the processing device (e.g., the acquisition module 602 of the processing device 540) may acquire, via one or more cameras, a plurality of image frames of the subject. The radar echo data may be used to characterize a rigid motion (i.e., the first motion mentioned above) of the subject. In some embodiments, the one or more cameras may be installed at suitable positions on or in the vicinity of the medical device in order to capture the plurality of image frames for identifying the rigid motion of the subject. In some embodiments, the plurality of image frames may be stored in a storage device (e.g., the storage device 550).

In 1208, the processing device (e.g., the reconstruction module 610 of the processing device 540) may generate an image based on the scan data, the radar echo data, and the plurality of image frames (operation 1008).

In some embodiments, the medical device may acquire the scan data continuously according to a retrospective gating technique. The reconstruction module 610 may obtain reconstruction data from the scan data based on the radar echo data and the plurality of image frames. However, in some embodiments, the one or more radars may detect both the physiological motion (i.e., the second motion) and the rigid motion (i.e., the first motion) if there exists the rigid motion during the scan. In this case, if the radar echo data without a correction is used to determine physiological motion related data directly, the determined physiological motion related data may be inaccurate because the radar echo data includes disturbed information caused by the rigid motion. To resolve this issue, the radar echo data may be corrected based on the plurality of image frames.

Specifically, the first data determination module 604 of the processing device 540 may determine, based on at least a part of the plurality of image frames, first data regarding the first motion (i.e., rigid motion related data). The first data may include one or more motion parameters of the rigid motion of the subject. The second data determination module 606 of the processing device 540 may correct the radar echo data according to the one or more motion parameters of the rigid motion. The second data determination module 606 may extract, from the corrected radar echo data, second data including cardiac motion data (e.g., the ECG signal illustrated in FIG. 11) and/or respiratory motion data (e.g., the ECG signal illustrated in FIG. 10). More detailed descriptions of first data and second data may be found elsewhere in the present disclosure, see, e.g., FIG. 8 and the descriptions thereof, and not repeated herein.

In some embodiments, the reconstruction module 610 may obtain the reconstruction data from the scan data based on the cardiac motion data or the respiratory data. For example, the reconstruction module 610 may obtain scan data corresponding to one or more specific cardiac cycles. The one or more specific cardiac cycles may be identified based on the cardiac motion data (e.g., the ECG signal). The scan data corresponding to the specific cardiac cycles may be designated as the reconstruction data. The reconstruction module 610 may reconstruct the image based on the designated reconstruction data. As another example, the reconstruction module 610 may obtain scan data corresponding to one or more specific respiratory cycles (e.g., one or more expiration periods). The one or more specific respiratory cycles may be identified based on the respiratory motion data (e.g., the respiratory signal). The scan data corresponding to the specific respiratory cycles may be designated as the reconstruction data. The reconstruction module 610 may reconstruct the image based on the designated reconstruction data. It should be understood that the fuse of the radar echo data and the image frames may be assisted to determine accurate cardiac motion data and respiratory motion data. The accurate cardiac motion data and respiratory motion data may reduce or avoid motion artifacts (e.g., cardiac motion artifacts or respiratory motion artifacts) in the reconstructed image.

It should be noted that the description of the process 1200 is provided for the purposes of illustration, and not intended to limit the scope of the present disclosure. For persons having ordinary skills in the art, various variations and modifications may be conducted under the teaching of the present disclosure. For example, operations 1202 to 1206 may be integrated into a single operation, and/or be performed simultaneously. However, those variations and modifications may not depart from the protection of the present disclosure.

Figure 13:
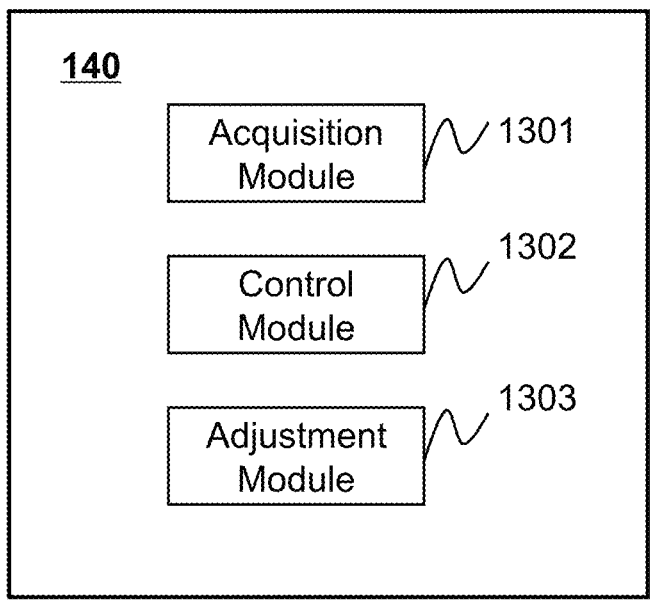
FIG. 13 is a block diagram illustrating another exemplary processing device according to some embodiments of the present disclosure.

FIG. 13 is a schematic diagram illustrating an exemplary processing device 120 according to some embodiments of the present disclosure. The processing device 120 may include an acquisition module 1301, a control module 1302, and an adjustment module 1303.

The acquisition module 1301 may be configured to obtain a plurality of sets of motion data each of which corresponds to one of a plurality of motion phases of the subject. The motion phases may relate to a physiological motion, such as a cardiac motion or a respiratory motion, which the subject may undergo during a treatment. A set of motion data corresponding to a motion phase may relate to motions of the subject during the motion phase. In some embodiments, the motion data corresponding to the motion phase may include first physiological motion data and/or second physiological motion data of the motion phase. In some embodiments, the acquisition module 1301 may be configured to obtain target physiological motion data reflecting the physiological motion of the subject during the radiation treatment or surgery. The target physiological motion data refers to physiological motion data of the subject that is currently (or almost current) collected or determined during the radiation treatment, which may reflect the physiological motion of the subject at the present (or almost the present). More descriptions regarding the obtaining of the sets of motion data and the target physiological data may be found elsewhere in the present disclosure. See, e.g., operations 1401 and 1403 and relevant descriptions thereof.

The control module 1302 may be configured to direct the radiotherapy device to deliver the radiation treatment to the subject according to the treatment plan. The treatment plan may describe how the radiation treatment is planned to be performed on the subject, more specifically, how one or more radiation beams are delivered to the subject during the radiation treatment. More descriptions regarding the delivery of the radiation treatment according to the treatment plan may be found elsewhere in the present disclosure. See, e.g., operation 1402 and relevant descriptions thereof.

The adjustment module 1303 may be configured to adjust the treatment plan to adapt to the physiological motion of the subject based on the target physiological motion data and the plurality of sets of motion data during the radiation treatment. In some embodiments, the adjustment module 1303 may determine, among the plurality of motion phases, a target motion phase of the subject based on the physiological motion data corresponding to the plurality of motion phases and the target physiological motion data. The adjustment module 1303 may further adjust the treatment plan to adapt to the physiological motion of the subject based on the target motion phase. More descriptions regarding the adjustment of the treatment plan may be found elsewhere in the present disclosure. See, e.g., operation 1404 and relevant descriptions thereof.

In some embodiments, the adjustment module 1303 may directly determine how to deliver the radiation treatment based on the target physiological motion data and the sets of motion data without adjusting the treatment plan. For example, a real-time position of the target of the subject may be determined based on the sets of motion data and the target physiological motion data. The adjustment module 1303 may control one or more components of the radiotherapy device (e.g., a couch and/or a gantry) to move so that the real-time position of the target can be targeted by a radiation beam.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may include one or more additional modules and/or one or more modules described above may be omitted. Additionally or alternatively, two or more modules may be integrated into a single module and/or a module may be divided into two or more units. However, those variations and modifications also fall within the scope of the present disclosure. In some embodiments, one or more modules of the processing device 120 may be integrated into the processing device 540, or the processing device 120 and the processing device 540 may share one or more same modules. For example, the acquisition module 1301 and the acquisition module 602 may be the same.

FIG. 14 is a flowchart illustrating an exemplary process for treating a subject according to some embodiments of the present disclosure. In some embodiments, process 1400 may be executed by the medical system 100. For example, the process 1400 may be implemented as a set of instructions (e.g., an application) stored in a storage device (e.g., the storage device 130, the storage device 550). In some embodiments, the processing device 120 (e.g., the processing device 540 of the medical imaging system 500 and/or one or more modules illustrated in FIG. 13) may execute the set of instructions and accordingly direct one or more components of the medical system 100 to perform the process 1400.

Radiotherapy is widely used in clinical treatment for cancers and other conditions. Conventionally, a treatment plan is usually generated for a subject before treatment starts. The subject may be a patient, a portion of a patient, or any organism that needs to be treated by a radiotherapy device (e.g., the medical device 110). Normally, the treatment plan may be performed for the subject during a treatment period of multiple days (e.g., 2 to 5 weeks) (e.g., by serval treatment sessions). However, during the treatment period, an anatomical change (e.g., weight loss, growth, shrinkage, or disappearance of a tumor, the appearance of a new tumor, etc.) may take place within the subject. The size and/or position of a certain organ may change between the time of planning and the time of delivering a radiation treatment (e.g., a specific treatment session). Accordingly, the treatment plan may need to be verified and/or updated before the radiation treatment starts or even during the treatment.

For example, an IGRT technique may be utilized. A scan (e.g., a CT scan or an MRI scan) may be performed before the radiation treatment to acquire an anatomical image of the subject, which may be used to verify whether the treatment plan of the subject needs to be adjusted. However, the adjustment of the treatment plan based on the IGRT technique can only compensate for anatomical changes of the subject and/or positioning errors that occur before the radiation treatment. During the radiation treatment of the subject, the subject may undergo a physiological motion (or referred to as a physiological motion or a second motion), such as a cardiac motion, a respiratory motion, a gastrointestinal motion, a skeletal muscle motion, or the like, or any combination thereof. Such physiological motion of the subject may affect the delivery accuracy of the treatment plan, and need to be tracked and compensated during the radiation treatment, so as to ensure that a radiation beam delivered to the subject matches a planned dose distribution as closely as possible.

Some existing physiological motion tracking techniques may utilize an MRI-RT device to perform an MRI scan and a radiation treatment simultaneously on the subject, but the MRI-RT device and the radiation treatment performed using the MRI-RT device are expensive. Some other physiological motion tracking techniques try to collect surface motion data during the radiation treatment and estimate physiological motion data based on the surface motion data. However, the physiological motion tracking based on the surface motion data may have limited accuracy because of the inconsistency between the physiological motion and the surface motion of the subject, which may result in motion compensation errors and reduce the treatment precision. Therefore, it is desired to provide effective systems and methods for tracking the physiological motion of the subject during the radiation treatment. In some embodiments, the physiological motion of the subject may be tracked by performing the following operations of the process 1400.

In 1401, the processing device 120 (e.g., the acquisition module 1301) may obtain a plurality of sets of motion data each of which corresponds to one of a plurality of motion phases of the subject.

The motion phases may relate to a physiological motion, such as a cardiac motion or a respiratory motion, that the subject may undergo during a treatment. For example, a cardiac cycle may include systole (during which the left and right ventricles contract and eject blood into the aorta and pulmonary artery, respectively) and diastole (during which the ventricles are relaxed). The cardiac cycle may be divided into a plurality of cardiac phases, such as 5 or 10 cardiac phases depending on, for example, the heart rate and/or movement amplitude of the heart. As another example, a respiratory cycle may include an inspiratory phase (during which the chest of the subject expands and air flows into the lungs) and an expiratory phase (during which the chest shrinks and the air is pushed out of the lungs). The respiratory cycle may be gated into a plurality of respiratory phases, such as 4 respiratory phases including a mid-inspiratory phase, an end-inspiratory phase, a mid-expiratory phase, and an end-expiratory phase according to, for example, time or the amplitude of the respiratory motion.

A set of motion data corresponding to a motion phase may relate to motions of the subject during the motion phase. In some embodiments, the motion data corresponding to the motion phase may include first physiological motion data and/or second physiological motion data of the motion phase. The first physiological motion data may be collected via a medical imaging device and reflect the physiological motion of the subject during the motion phase. For example, the first physiological motion data may indicate the position, the moving velocity, the moving direction, the displacement, etc., or any combination thereof, of one or more internal organs or tissue of the subject that may move due to the physiological motion during the motion phase. As used herein, if a set of data is collected by a device or determined based on data collected by the device, the set of data may be deemed as being collected via or using the device.

In some embodiments, the first physiological motion data of a motion phase may be collected or determined by performing a scan on the subject using the medical imaging device. Exemplary first physiological motion data may include scan data of the subject acquired by the medical imaging device during the motion phase in the scan, a medical image corresponding to the motion phase reconstructed based on the scan data, position parameter(s) of one or more internal organs or tissue of the subject during the motion phase determined based on the scan data, motion parameter(s) of the internal organ(s) or tissue of the subject during the motion phase determined based on the scan data, or the like, or any combination thereof.

For example, the first physiological motion data of the motion phase may include an MRI image corresponding to the motion phase, which is reconstructed based on MRI data of the subject acquired by an MRI device during the motion phase. As another example, the first physiological motion data of the motion phase may include a motion vector field between the motion phase and a reference motion phase. The motion vector field between the motion phase and the reference motion phase may include one or more motion vectors corresponding to one or more physical points of the subject, wherein a motion vector of a physical point may describe a motion of the physical point between the motion phase and the reference motion phase. In some embodiments, the first physiological motion data acquired or determined by performing a scan on the subject using a medical imaging device may be also referred to as scan-based physiological motion data. For the convenience of descriptions, the terms "physiological motion data" and "scan-based physiological motion data" are collectively referred to as physiological motion data unless the context clearly indicates otherwise.

The second physiological motion data may be collected via a first motion sensor and reflect the physiological motion of the subject during the motion phase. In some embodiments, the second physiological motion data of a motion phase may include surface motion data that reflects the surface motion of the subject during the motion phase, wherein the surface motion may be induced by the physiological motion inside the subject. For example, the surface motion data may indicate the position, the moving velocity, the moving direction, the displacement, etc., or any combination thereof, of the body surface near the one or more internal organs or tissue of the subject that may move due to the physiological motion during the motion phase. Taking the respiratory motion as an example, a set of motion data corresponding to a respiratory phase may include first physiological motion data relating to the lungs, the thoracic and abdominal cavity, and/or the liver of the subject, and the surface motion data relating to the body surface of the chest and the abdomen of the subject.

In some embodiments, the surface motion data of a motion phase may be collected via the first motion sensor.

Exemplary surface motion data of the motion phase include sensor data (e.g., radar echo data, image data, depth data, position data) collected by the first motion sensor during the motion phase, position parameter(s) of the body surface of the subject (or a portion thereof) determined based on the sensor data, motion parameter(s) of the body surface of the subject (or a portion thereof) determined based on the first motion sensor, or the like, or any combination thereof. For example, the surface motion data of the motion phase may include a plurality of image frames collected by one or more cameras during the motion phase and/or radar echo data collected by one or more radar sensors during the motion phase. As another example, the surface motion data of the motion phase may include a moving direction and/or a moving distance of one or more physiological points on the body surface of the subject, which is (are) determined based on the image frames and/or the radar echo data. Exemplary first motion sensors may include a radar sensor, an optical sensor, a ranging device, a TOF device, a structured light scanner, a camera, or the like, or any combination thereof.

Additionally or alternatively, the second physiological motion data of a motion phase may include a physiological signal of the subject collected via the first motion sensor during the motion phase. For example, the second physiological motion data may include an ECG signal collected by an ECG sensor or a radar sensor (e.g., a radar having a low-frequency range as described in connection with FIG. 2) during the motion phase. In some embodiments, the first motion sensor may include a radar sensor configured to collect radar echo data from the subject. The second physiological motion data may include an ECG signal and/or a respiratory signal extracted from the radar echo data, e.g., by performing the process 800 as described in connection with FIG. 8.

In some embodiments, the sets of motion data may be collected before the delivery of the radiation treatment. For example, scan data and sensor data of the subject may be acquired simultaneously by the medical imaging device and the first motion sensor, respectively, during a scan of the subject performed before the radiation treatment. The processing device 120 may acquire the scan data and the sensor data from the medical imaging device and the first motion sensor, respectively, and determine the sets of motion data based on the scan data and the sensor data. Alternatively, the sets of motion data (or the scan data and the sensor data) may be stored in a storage device (e.g., the storage device 130, the storage device 550, or an external storage device). The processing device 120 may retrieve the sets of motion data (or the scan data and the sensor data) from the storage device. More descriptions regarding the obtaining of the sets of motion data may be found elsewhere in the present disclosure. See, e.g., FIG. 15 and relevant descriptions thereof.

In 1402, the processing device 120 (e.g., the control module 1302) may direct the radiotherapy device to deliver the radiation treatment to the subject.

In some embodiments, the radiation treatment may be delivered according to the treatment plan. The treatment plan may describe how the radiation treatment is planned to be performed on the subject, more specifically, how one or more radiation beams are delivered to the subject during the radiation treatment. For example, the treatment plan may include a dose plan (e.g., a total dose and/or a dose distribution) delivered to one or more ROIs, such as, a target and/or one or more organ at risks (OARs) of the subject, during the radiation treatment. The target refers to a certain anatomical structure that needs to be tracked and/or monitored during the radiation treatment. For example, the target may be a tumor, an organ with a tumor, a tissue with a tumor, or any combination thereof, that needs to be treated by radiations. An OAR may include an organ (or a portion thereof) and/or a tissue that are close to the target and not indented to be subjected to radiation but under the risk of radiation damage due to its proximity to the target.

In some embodiments, the treatment plan may be generated base on planning scan data. For example, before the subject begins to receive treatment (e.g., days or weeks before the treatment commences), the planning scan data of the subject may be acquired using a medical imaging device (e.g., the medical device 110). The treatment plan may be designed for the subject based on the planning scan data. In some embodiments, the planning scan data may be the same as or different from the scan data used to determine the first physiological motion data as described in operation 1401.

In some embodiments, the planning scan data may include a first portion and a second portion. The first portion of the planning scan data may be used to determine the dose plan delivered to the target and/or the OAR(s) of the subject during the radiation treatment. The second portion of the planning scan data may be used to determine contour information of the target and/or the OAR(s) of the subject. In some embodiments, the first portion of the planning scan data may include, for example, MRI data (e.g., an MRI image), CT data (e.g., a CT image), etc. The MRI data may be acquired by an MRI device. The CT data may include actual CT data acquired by a CT device or pseudo CT data generated based on the MRI data. For example, a pseudo CT image of the subject may be generated based on an MRI image of the subject using a machine learning model. The machine learning model may be any suitable machine learning model that is capable of transforming an MRI image or MRI data into a CT image, such as a trained generative adversarial network (GAN) model (e.g., a conditional GAN model). In some embodiments, the second portion of the planning scan data may include CT data, MRI data, PET data (e.g., a PET image), etc.

In some embodiments, the first portion and the second portion of the planning scan data may be the same data or different data. For example, the first portion and the second portion of the planning scan data may be the same set of MRI data of the subject. As another example, the first portion may include a CT image of the subject, and the second portion may include a PET image of the subject. In some embodiments, the first portion and the second portion of the planning scan data may be collected by the same medical imaging device (e.g., a single modality scanner or a multi-modality scanner) or different medical imaging devices.

In 1403, during the radiation treatment, the processing device 120 (e.g., the acquisition module 1301) may obtain target physiological motion data reflecting the physiological motion of the subject, wherein the target physiological motion data may be collected via a second motion sensor.

The target physiological motion data refers to physiological motion data of the subject that is currently (or almost current) collected via the second motion sensor during the radiation treatment, which may reflect the physiological motion of the subject at the present (or almost the present). In some embodiments, the target physiological motion data may include a target physiological signal collected by, for example, a cardiac sensor, a respiratory sensor, a radar having a low frequency range, etc., during the radiation treatment. In some embodiments, the target physiological motion data may include target surface motion data reflecting the surface motion induced by the physiological motion of the subject during the radiation treatment. For example, during the radiation treatment, the processing device 120 may transmit an instruction to the second motion sensor to collect surface motion data of the subject. In response to the instruction, the second motion sensor may collect surface motion data of the subject as the target surface motion data and transmit the target surface motion data to the processing device 120 directly or via a network (e.g., the network 150). As another example, the second motion sensor may be directed to collect surface motion data of the subject during the radiation treatment continuously or intermittently (e.g., periodically). After the second motion sensor collects surface motion data, the second motion sensor may transmit the surface motion data to the processing device 120 as the target surface motion data for further analysis.

In some embodiments, the collection of the target physiological motion data by the second motion sensor, the transmission of the collected target physiological motion data to the processing device 120, and the analysis of the target physiological motion data may be performed substantially in real time so that the target physiological motion data may provide information indicating a substantially real-time status of the subject. In some embodiments, the second motion sensor may be configured to collect target sensor data during the radiation treatment, and the target physiological motion data may be determined based on the target sensor data collected during the radiation treatment by the processing device 120 or another computing device.

In some embodiments, the first motion sensor for collecting the second physiological motion data as described in operation 1401 and the second motion sensor for collecting the target physiological motion data may be the same device or different devices of a same type. For example, the second motion sensor and the first motion sensor may both be radar sensors. Alternatively, the first motion sensor and the second motion sensor may be of different types of motion sensors. For example, the second motion sensor may be a radar sensor, and the first motion sensor may be an optical sensor. In some embodiments, the first motion sensor and the second motion sensor may be placed at the same or substantially same position relative to the subject to collect the surface motion data and the target surface motion data. In this way, the second physiological motion data and the target physiological motion data may be collected from the same or substantially same perspective with respect to the subject, which may reduce or eliminate the effect of the difference between the perspectives of the second physiological motion data and the target physiological motion data on the physiological motion tracking, thereby improving the accuracy of the physiological motion tracking.

In some embodiments, the surface motion of the subject during the radiation treatment may be caused by the physiological motion and also a rigid motion of the subject. The target surface motion data may include a disturbed portion caused by the rigid motion of the subject during the radiation treatment, which needs to be corrected and/or removed. In some embodiments, the target surface motion data may be corrected by performing one or more operations of process 1600 as described in connection with FIG. 16.

In 1404, during the radiation treatment, the processing device 120 (e.g., the adjustment module 1303) may adjust the treatment plan to adapt to the physiological motion of the subject based on the target physiological motion data and the plurality of sets of motion data.

In some embodiments, the radiation treatment may be delivered according to a treatment plan as described in connection with operation 1402. The processing device 120 may adjust the treatment plan to adapt to the physiological motion of the subject based on the target physiological motion data and the sets of motion data. Alternatively, the processing device 120 may directly determine how to deliver the radiation treatment based on the target physiological motion data and the sets of motion data without adjusting the treatment plan.

In some embodiments, the processing device 120 may determine, among the plurality of motion phases, a target motion phase of the subject based on the second physiological motion data corresponding to the plurality of motion phases and the target physiological motion data. The target motion phase refers to an estimated current motion phase of the subject (e.g., when the target physiological motion data or the corresponding target sensor data is collected by the second motion sensor). The processing device 120 may further adjust the treatment plan to adapt to the physiological motion of the subject based on the target motion phase.

For example, the second physiological motion data may include surface motion data of the subject, and the target physiological motion data may include target surface motion data of the subject. The processing device 120 may select the target motion phase among the motion phases by comparing the target surface motion data with the surface motion data of each of the motion phases. In some embodiments, the comparison result between the target surface motion data and surface motion data of a motion phase may include any metrics for measuring the extent of similarity (or also referred to as a similarity degree) between the target surface motion data and the surface motion data. The similarity degree between the target surface motion data and the surface motion data corresponding to the motion phase may be determined based on a similarity algorithm, such as, an image similarity algorithm, a peak signal to noise ratio (PSNR) algorithm, a structural similarity (SSIM) algorithm, a perceptual hash algorithm, a cosine similarity algorithm, a histogram-based algorithm, a Euclidean distance-based algorithm, or the like, or any combination thereof.

Merely by way of example, the processing device 120 may determine a similarity degree between the target surface motion data and the surface motion data of each motion phase. The processing device 120 may further select, among the motion phases, a motion phase whose surface motion data has the highest similarity degree to the target surface motion data. The processing device 120 may then designate the selected motion phase as the target motion phase of the subject.

In some embodiments, the processing device 120 may determine first sensor-based physiological motion data of the motion phases based on the surface motion data of the motion phases. The processing device 120 may also determine second sensor-based physiological motion data based on the target surface motion data, and determine the target motion phase based on the first and second sensor-based physiological motion data. Merely by way of example, the processing device 120 may extract a first respiratory waveform from radar echo data collected by a radar sensor before the radiation treatment in a plurality of respiratory phases over a respiratory cycle of the subject. The first respiratory waveform may be determined, e.g., by performing process 800 as described in connection with FIG. 8. The first respiratory waveform may include a plurality of portions corresponding to the plurality of respiratory phases of the subject. The processing device 120 may also extract a second respiratory waveform from radar echo data collected by the radar sensor in a current period during the radiation treatment. Further, the processing device 120 may determine a target respiratory phase (i.e., a respiratory phase of the subject in the current period) based on the first respiratory waveform and the second respiratory waveform.

Merely by way of example, a portion of the first respiratory waveform that is similar to the second respiratory waveform may be identified using an identification technique (e.g., an image identification technique, a machine learning technique, etc.). The respiratory phase corresponding to the identified portion in the first respiratory waveform may be designated as the target respiratory phase of the subject. In some embodiments, the first sensor-based physiological motion data may be determined by the first motion sensor or another computing device, the processing device 120 may obtain the first sensor-based physiological motion data from the first motion sensor or another computing device. Additionally or alternatively, the second sensor-based physiological motion data may be determined by the second motion sensor or another computing device, the processing device 120 may obtain the second sensor-based physiological motion data from the second motion sensor or another computing device.

In some embodiments, the first motion sensor and the second motion sensor may be different types of motion sensors, and the processing device 120 may need to pre-process the second physiological motion data and the target physiological motion data before determining the target motion phase. Merely by way of example, the first motion sensor may be an ECG sensor configured to acquire ECG signals during the motion phases, while the second motion sensor may be a camera configured to capture image data during the radiation treatment. The processing device 120 may need to estimate a target ECG signal representing the cardiac motion of the subject during the radiation treatment based on the image data, and further determine the target motion phase based on the ECG signals and the target ECG signal.

After the target motion phase is determined, the processing device 120 may adjust the treatment plan to adapt to the physiological motion of the subject based on the target motion phase. For example, the first physiological motion data corresponding to the target motion phase (referred to as target data for brevity hereinafter) may be determined. The processing device 120 may further adjust the treatment plan to adapt to the physiological motion of the subject based on the target data. The target data may be regarded as predicted physiological motion data that is collected via the medical imaging device and reflects a current physiological motion of the subject (e.g., when the target surface motion data is collected by the second motion sensor).

In some embodiments, the processing device 120 may determine position information of one or more ROIs (e.g., the target and/or the OAR(s)) of the subject during the target motion phase based on the target data. The position information of an ROI (e.g., the target) may indicate a position and/or a motion of the ROI at the time when the target physiological motion data is collected, e.g., at the present moment (or substantially at the present moment). For example, the target data may include a target MRI image of the subject corresponding to the target motion phase. The processing device 120 may identify a portion representing the target from the target MRI image using an image identification technique (e.g., an image segmentation technique), and determine the position of the target based on identified portion. Exemplary image segmentation techniques may include a region-based segmentation technique, an edge-based segmentation technique, a wavelet transform segmentation technique, a mathematical morphology segmentation technique, a machine learning-based segmentation technique (e.g., using a trained segmentation model), a genetic algorithm-based segmentation technique, or the like, or a combination thereof. As another example, the target data may include a motion vector field between the target motion phase and the reference motion phase. The processing device 120 may determine one or more motion parameters (e.g., a moving direction, a moving distance) of the ROI(s) of the subject based on the motion vector field.

Then, the processing device 120 may adjust the treatment plan to adapt to the physiological motion of the subject based on the position information of the ROI(s). In some embodiments, the processing device 120 may direct the radiotherapy device to gate a delivery of a radiation beam according to the position information of the ROI(s). As used herein, "gating a delivery of a radiation beam" may refer to turning on and/or off the radiation beam during the radiation treatment. For example, the radiation beam may be turned on only when an ROI is at a certain position during a specific interval of a motion cycle of the ROI.

Taking a lung as an exemplary target to be treated, the lung may undergo a respiratory motion during the radiation treatment and need to be tracked to facilitate an accurate delivery of the radiation beam to the lung. A specific segment in a respiratory cycle (also referred to as a gate window in the respiratory cycle), during which the respiratory motion amplitude (or amount) of the lung may be minimal or below a threshold, may be determined. The gate window and the position information may be used to determine when the radiotherapy device (e.g., the LINAC of the radiotherapy device) needs to deliver the radiation beam toward the lung during the radiation treatment. For example, the position information of the lung may be used to determine whether the lung is within the gate window at the present moment (or substantially the present moment). If the lung is within the gate window, the radiation beam may be delivered to the lung according to the position information of the lung. If the lung is outside of the gate window, the delivery of the radiation beam toward the lung may be turned off. In some embodiments, whether the lung is within the gate window may be determined by determining whether the target motion phase is within the gate window. For example, if the target motion phase is within the gate window, the lung may be deemed as within the gate window.

In some embodiments, the delivery of the radiation beam may be turned on or off by turning on or off a treatment radiation source of the radiotherapy device. In some embodiments, the treatment radiation source may remain on during a radiation treatment, while the delivery of the radiation beam toward the lung may be turned on or off, or the location/shape of the treatment beam aperture may be modified, or the radiation output rate may be modified, by adjusting one or more collimators or radiation power controls of the radiotherapy device.

Additionally or alternatively, the processing device 120 may direct the radiotherapy device to aim the radiation beam at the target of the subject according to the position information of the ROI(s). For example, the position information of the ROI(s) may include position information of the target, and the radiation beam may be caused to aim at the target (e.g., an isocenter of the target) based on the position information of the target. As another example, the position information of the ROI(s) may include position information of an OAR adjacent to the target, the processing device 120 may direct the radiotherapy device to aim the radiation beam at the target and avoid irradiating the OAR. In some embodiments, the processing device 120 may send an instruction to the radiotherapy device to control the movement and/or shape of one or more components of the radiotherapy device (e.g., a gantry, a collimator, a couch), so as to control the radiation beam to aim at the target. By gating the radiation beam and/or aiming the radiation beam at the target, the radiation beam may be delivered to the target more precisely during the radiation treatment, thereby reducing or avoiding an impact on a surrounding healthy organ or tissue by radiation treatment.

According to some embodiments of the present disclosure, prior reference information including a plurality of sets of motion data corresponding to a plurality of motion phases may be collected in advance before a radiation treatment of the subject. The prior reference information may indicate a corresponding relationship between first physiological motion data collected via the medical imaging device and second physiological motion data (e.g., surface motion data) collected via the first motion sensor of a same motion phase. Based on the prior reference information and target physiological motion data collected during the radiation treatment, the physiological motion of the subject can be tracked timely (e.g., in substantially real-time) and efficiently (e.g., without performing complex analysis for estimating physiological motion based on the target surface motion data).

In some embodiments, the second physiological motion data and the target physiological motion data may be collected using one or more motion sensors (e.g., radar sensors and/or cameras). The motion sensor(s) may have a low production cost, and can be easily mounted on or integrated into existing radiotherapy devices and/or medical imaging devices. Compared with conventional physiological motion tracking techniques that utilize an expensive MRI-RT device, the physiological motion tracking technique disclosed herein may be more cost-effective and generally applicable.

In addition, in some embodiments, the first physiological motion data may be generated based on scan data (e.g., the MRI data, the CT data, etc.) of the subject that include accurate anatomical information about the internal structure of the subject. Compared with traditional physiological motion data estimated from surface motion data of the subject, the scan-based physiological motion data used in the present disclosure can reflect the physiological motion of the subject more accurately and avoid the effect of the inconsistency existing between the physiological motion and the surface motion of the subject. The physiological motion tracking performed based on the scan-based physiological motion data may have an improved accuracy, and the treatment plan can be adjusted to adapt to the physiological motion of the subject during radiation treatment in a more timely and accurate manner.

It should be noted that the above description regarding the process 1400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1400 may be accomplished with one or more additional operations not described and/or without one or more of the operations discussed above.

For example, operations 1401 and 1402 may be performed simultaneously, or operation 1402 may be performed before operation 1401. As another example, the processing device 120 may store information and/or data (e.g., the plurality of sets of motion data, the treatment plan, the target physiological motion data, the position information of the target, etc.) in a storage device (e.g., the storage device 130) disclosed elsewhere in the present disclosure. In some embodiments, operations 1403 and 1404 may be performed continuously or intermittently (e.g., periodically) in the radiation treatment to track the physiological motion of the subject in the radiation treatment.

Figure 15:
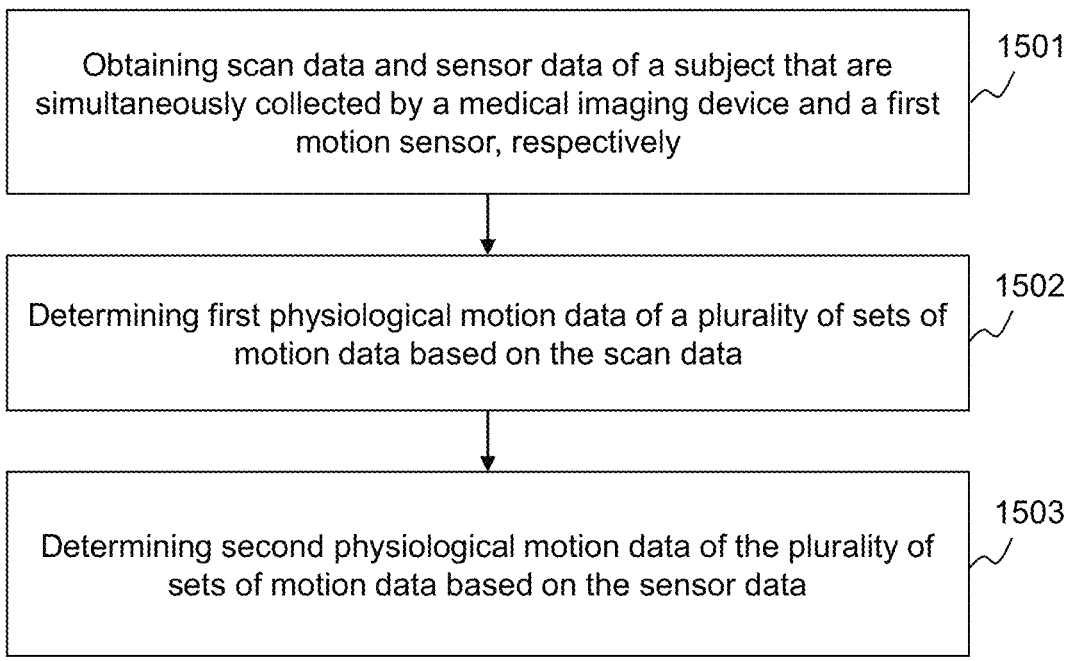
FIG. 15 is a flowchart illustrating an exemplary process for obtaining a plurality of sets of motion data according to some embodiments of the present disclosure.

FIG. 15 is a flowchart illustrating an exemplary process for obtaining a plurality of sets of motion data according to some embodiments of the present disclosure. In some embodiments, one or more operations of process 1500 may be performed to achieve at least part of operation 1401 as described in connection with FIG. 14.

In 1501, the processing device 120 (e.g., the acquisition module 1301) may obtain scan data and sensor data of the subject.

The scan data and the sensor data may be simultaneously collected by a medical imaging device (e.g., a CT device, an MRI device, a PET device) and a first motion sensor (e.g., a radar sensor), respectively, before the radiation treatment. For example, before the radiation treatment, the medical imaging device may be directed to collect the scan data by performing a scan on the subject, and at the same time, the first motion sensor may be directed to collect the sensor data during the scan. More descriptions regarding a medical imaging device and a motion sensor may be found elsewhere in the present disclosure. See, e.g., FIG. 1 and relevant descriptions thereof.

The scan data may be used to determine first physiological motion data reflecting a physiological motion of the subject during a plurality of motion phases. The sensor data of the subject may be used to determine second physiological motion data reflecting the physiological motion of the subject during the motion phases, such as surface motion data reflecting a surface motion induced by the physiological motion of the subject during the motion phases. In some embodiments, the scan data may include a plurality of sets of scan data each of which corresponds to one of the motion phases of the subject. Additionally or alternatively, the sensor data may include a plurality of sets of sensor data each of which corresponds to one of the motion phases of the subject. Merely by way of example, during the scan of the subject, a respiratory sensor may be used to detect a respiratory signal of the subject. As another example, the sensor data collected during the scan may be used to estimate a respiratory signal of the subject. The scan data and the sensor data may be sorted into the sets of scan data and the sets of sensor data, respectively, based on the detected or estimated respiratory signal.

In some embodiments, the processing device 120 may acquire the scan data and the sensor data from the medical imaging device and the first motion sensor, respectively. Alternatively, the scan data and the sensor data may be stored in a storage device (e.g., the storage device 130, the storage device 550, or an external storage device). The processing device 120 may retrieve the scan data and the sensor data from the storage device.

In 1502, the processing device 120 (e.g., the acquisition module 1301) may determine the first physiological motion data of the plurality of sets of motion data based on the scan data.

In some embodiments, for each of the motion phases of the subject, the processing device 120 may reconstruct a medical image (e.g., an MRI image) of the subject corresponding to the motion phase based on the set of scan data corresponding to the motion phase. For example, the medical image of the subject corresponding to a motion phase may be reconstructed using one or more reconstruction algorithms. Exemplary reconstruction algorithms may include a rapid reconstruction algorithm, an algebraic reconstruction algorithm, an iteration reconstruction algorithm, a back projection reconstruction algorithm, or the like, or any combination thereof. Exemplary rapid reconstruction algorithms may include a fast Fourier transform algorithm, a compressed sensing algorithm, a deep learning algorithm, or the like, or any combination thereof.

For each of the motion phases of the subject, the processing device 120 may then determine the first physiological motion data of the motion phase based on the medical image corresponding to the motion phase. For example, the medical image corresponding to the motion phase may be directly used as the first physiological motion data of the motion phase. As another example, based on the medical image corresponding to the motion phase and optionally medical image(s) corresponding to other motion phase(s), the processing device 120 may determine one or more position parameters (e.g., a coordinate) and/or motion parameters (e.g., a moving displacement, a moving direction, etc.) of the subject or a portion of the subject (e.g., a target) as the first physiological motion data of the motion phase.

In some embodiments, for each motion phase, the processing device 120 may determine a motion vector field between the motion phase and a reference motion phase among the motion phases based on the medical image corresponding to the motion phase and a medical image corresponding to the reference motion phase. For each motion phase, the processing device 120 may further designate the motion vector field of the motion phase as the first physiological motion data of the motion phase.

The reference motion phase may be any motion phase selected from the motion phases of the subject. For example, the reference motion phase may be selected from the motion phases according to a default setting of the medical system 100 or by a user manually. As another example, the reference motion phase may be selected according to a specific rule, e.g., the end-expiratory phase in which the respiratory motion of the subject is relatively smooth may be selected as a reference motion phase for the respiratory motion.

The motion vector field between a motion phase and the reference motion phase may describe the motion of a plurality of physical points of the subject from the motion phase to the reference motion phase or from the reference motion phase to the motion phase. For example, the motion vector field may include a plurality of motion vectors corresponding to the plurality of physical points of the subject. Merely by way of example, a specific physical point may correspond to a first pixel or voxel having a first coordinate in the medical image of the motion phase, and a second pixel or voxel having a second coordinate in the medical image of the reference motion phase. The motion vector of the specific physical point may be determined based on the first coordinate and the second coordinate (e.g., as a vector from the first coordinate to the second coordinate).

In some embodiments, the motion vector field between a motion phase and the reference motion phase may be determined by registering the medical image of the motion phase with the medical image of the reference motion phase using an image registration algorithm (e.g., an image registration algorithm as described in connection with FIG. 7).

In 1503, the processing device 120 (e.g., the acquisition module 1301) may determine the second physiological motion data of the plurality of sets of motion data based on the sensor data.

In some embodiments, for each of the motion phases, the processing device 120 may designate the set of sensor data corresponding to the motion phase as the second physiological motion data corresponding to the motion phase. In other words, the second physiological motion data of a motion phase may include the original sensor data collected by the first motion sensor during the motion phase. For example, the second physiological motion data of a motion phase may include radar echo data collected by a radar sensor during the motion phase.

In some embodiments, the second physiological motion data of the motion phases may be determined by processing the sensor data. For example, a plurality of images corresponding to a motion phase may be captured by a camera. One or more position parameters (e.g., a coordinate) and/or motion parameters (e.g., a moving displacement, a moving direction, etc.) of the body surface of the subject may be determined based on the plurality of images.

It should be noted that the above description regarding the process 1500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1500 may be accomplished with one or more additional operations not described and/or without one or more of the operations discussed above. For example, operations 1501 and 1502 may be performed simultaneously, or operation 1502 may be performed before operation 1501.

In some embodiments, the determination of the first physiological motion data based on the scan data may be performed by the medical imaging device (e.g., a processor of the medical imaging device). The processing device 120 may directly obtain the first physiological motion data of the sets of motion data from the medical imaging device. Additionally or alternatively, the determination of the second physiological motion data based on the sensor data may be performed by the first motion sensor, and the processing device 120 may directly obtain the second physiological motion data from the first motion sensor.

FIG. 16 is a flowchart illustrating an exemplary process for adjusting a treatment plan of a subject according to some embodiments of the present disclosure. In some embodiments, one or more operations of process 1600 may be performed during the radiation treatment of the subject to achieve at least part of operation 1404 as described in connection with FIG. 14. During the radiation treatment, target surface motion data of the subject may be obtained. In some occasions, the surface motion of the subject reflected by the target surface motion data may be caused by the physiological motion (e.g., the cardiac motion) as well as the rigid motion of the subject during the radiation treatment. The target surface motion data may need to be corrected to eliminate or reduce the effect of the rigid motion of the subject during the radiation treatment.

In 1601, the processing device 120 (e.g., the acquisition module 1301) may obtain target rigid motion data reflecting a rigid motion of the subject during the radiation treatment.

The rigid motion may include a translational and/or rotational motion of the subject. Exemplary rigid motions may include a pose motion of the subject, such as the rotating or nodding of the head of the subject, leg motion, hand motion, and so on. The target rigid motion data refers to rigid motion data of the subject that is currently collected or determined during the radiation treatment, which reflects the rigid motion of the subject at the present time (or almost the present time). In some embodiments, the rigid motion data may include one or more motion parameters relating to the rigid motion. The rigid motion data may be collected via one or more third motion sensors, such as one or more cameras, during the radiation treatment. A third motion sensor may be of the same device as or a different device from the second motion sensor for collecting the target surface motion data. In some embodiments, the collection of the rigid motion data and the collection of the target surface motion data may be performed simultaneously or substantially simultaneously during the radiation treatment. In some embodiments, the obtaining of the target rigid motion data may be performed in a similar manner as that of the first data as described in connection with operation 702, and the descriptions thereof are not repeated here.

In 1602, the processing device 120 (e.g., the control module 1302) may correct the target surface motion data based on the rigid motion data.

For example, the target surface motion data may include target radar echo data collected by a radar sensor, and the processing device 120 may correct the target radar echo data based on the target rigid motion data. The correction of the target radar echo data based on the target rigid motion data may be performed in a similar manner as the correction of the radar echo data based on the first data as described in connection with FIG. 8, and the descriptions thereof are not repeated here.

In 1603, the processing device 120 (e.g., the adjustment module 1303) may adjust the treatment plan to adapt to the physiological motion of the subject based on the corrected target surface motion data and the plurality of sets of motion data.

The adjustment of the treatment plan based on the corrected target surface motion data and the sets of motion data may be performed in a similar manner as that based on the target surface motion data and the sets of motion data as described in connection with operation 1404. For example, the processing device 120 may determine, among the motion phases, the target motion phase of the subject based on the corrected target surface motion data and the surface motion data corresponding to the motion phases. The processing device 120 may further adjust the treatment plan to adapt to the physiological motion of the subject based on the first physiological motion data corresponding to the target motion phase. In this way, a disturbed component of the target surface motion data caused by the rigid motion may be corrected or removed, which may improve the accuracy of the physiological motion tracking performed based on the corrected target surface motion data, and the treatment accuracy and effect.

It should be noted that the above description regarding the process 1600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1600 may be accomplished with one or more additional operations not described and/or without one or more of the operations discussed above.

In some embodiments, in the scan for collecting the sets of motion sensor before the radiation treatment, rigid motion data reflecting the rigid motion of the subject during the scan may be collected, e.g., using one or more cameras. The rigid motion data may include a set of rigid motion data in each of the motion phases of the subject. For each motion phase, the processing device 120 may correct the surface motion data of the motion phase based on the set of rigid motion data of the motion phase. In 1603, the processing device 120 may adjust the treatment plan based on the corrected target surface motion data, the first physiological motion data of the sets of motion data, and the corrected surface motion data of the sets of motion data. In this way, the rigid motion of the subject in both the scan and the radiation treatment may be taken into consideration, and the accuracy of the physiological motion tracking may be further improved.

FIG. 17 is a flowchart illustrating an exemplary process for treating a subject according to some embodiments of the present disclosure.

Figure 19:
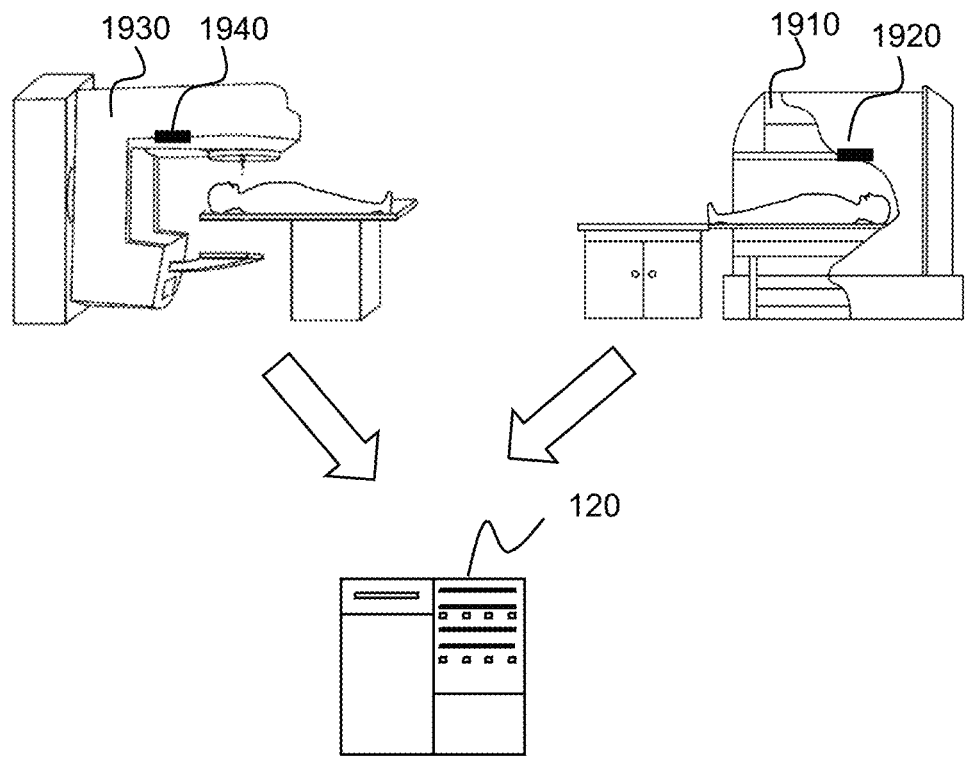
FIG. 19 is a schematic diagram illustrating an exemplary medical system according to some embodiments of the present disclosure.

In some embodiments, process 1700 may be executed by a medical system 1900 as shown in FIG. 19. As shown in FIG. 19, the medical system 1900 may include an MRI device 1910, a first motion sensor 1920, a radiotherapy device 1930, a second motion sensor 1940, and a processing device 120. The MRI device 1910 may be configured to acquire scan data (i.e., MRI data) of a subject by performing a medical scan (i.e., an MRI scan) on the subject before a radiation treatment of the subject. The first motion sensor 1920 may be configured to acquire sensor data relating to a physiological motion of the subject during the medical scan of the subject. The RT device 1930 may be configured to deliver a radiation treatment to the subject according to a treatment plan. The second motion sensor 1940 may be configured to acquire target sensor data relating to the physiological motion of the subject during the radiation treatment. The processing device 120 may be configured to adjust the treatment plan to adapt to the physiological motion of the subject during the radiation treatment based on the scan data, the sensor data, and the target sensor data.

In some embodiments, the MRI device 1910 and the radiotherapy device 1930 may be located in the same examination room or different examination rooms. In some embodiments, the first motion sensor 1920 may be mounted on the MRI device 1910, and the second motion sensor 1940 may be mounted on the radiotherapy device 1930 as shown in FIG. 19. In some alternative embodiments, the first motion sensor 1920 may be mounted on another position, for example, the ceiling of the examination room where the MRI device 1910 is located or a supporting device of the first motion sensor 1920. Additionally or alternatively, the second motion sensor 1940 may be mounted on another position, for example, the ceiling of the examination room where the radiotherapy device 1930 is located or a supporting device of the second motion sensor 1940. In some embodiments, the first motion sensor 1920 may be integrated into the MRI device 1910, and/or the second motion sensor 1940 may be integrated into the radiotherapy device 1930.

In 1701, the processing device 120 (e.g., the acquisition module 1301) may obtain MRI data and sensor data that are simultaneously collected via the MRI device 1910 and the first motion sensor 1920 during an MRI scan of the subject, respectively. The sensor data may relate to a physiological motion of the subject during the MRI scan.

For example, before a radiation treatment of the subject, the MRI device 1910 may be directed to acquire the MRI data of the subject by performing the MRI scan on the subject, and the first motion sensor 1920 may be directed to acquire the sensor data during the MRI scan of the subject. In some embodiments, the sensor data may include surface motion data that reflects a surface motion of the subject during the MRI scan, wherein the surface motion may be induced by the physiological motion of the subject. In some embodiments, operation 1701 may be performed in a similar manner as operation 1501, and the descriptions thereof are not repeated here.

In 1702, the processing device 120 (e.g., the control module 1302) may direct a radiotherapy device to deliver a radiation treatment to the subject according to a treatment plan.

In some embodiments, the processing device 120 may generate a pseudo CT image of the subject based on the MRI data. For example, the processing device 120 may generate the pseudo CT image using a generative adversarial network (GAN) model. The processing device 120 may further generate the treatment plan based on the pseudo CT image of the subject. In some embodiments, the processing device 120 may generate the treatment plan based on other planning scan data of the subject, e.g., a CT image acquired by a CT scan, a PET image acquired by a PET scan, or the like, or any combination thereof. More descriptions regarding the treatment plan may be found elsewhere in the present disclosure. See, e.g., operation 1402 and relevant descriptions thereof.

In 1703, during the radiation treatment, the processing device 120 (e.g., the acquisition module 1301) may obtain target sensor data relating to the physiological motion of the subject collected via the second motion sensor 1940.

The target sensor data of the subject refers to sensor data that is currently (or almost current) collected via the second motion sensor during the radiation treatment, which may be used to determine target physiological motion data of the subject. More descriptions regarding the target physiological motion data may be found elsewhere in the present disclosure. See, e.g., operation 1403 and relevant descriptions thereof. In some embodiments, the first motion sensor 1920 and the second motion sensor 1940 may be of the same type or different types. More descriptions regarding a first motion sensor and a second motion sensor may be found elsewhere in the present disclosure. See, e.g., FIG. 14 and relevant descriptions thereof.

In 1704, during the radiation treatment, the processing device 120 (e.g., the adjustment module 1303) may adjust the treatment plan to adapt to the physiological motion of the subject based on the target sensor data, the MRI data, and the sensor data.

In some embodiments, for each motion phase of the subject, the processing device 120 may determine first physiological motion data reflecting the physiological motion of the subject during the motion phase based on the MRI data, and determine second physiological motion data reflecting the physiological motion of the subject during the motion phase based on the sensor data. The processing device 120 may further determine the target physiological motion data reflecting the physiological motion of the subject during the radiation treatment based on the target sensor data. More descriptions regarding the determination of the first physiological motion data and the second physiological motion data may be found elsewhere in the present disclosure. See, e.g., operation 1401 and FIG. 15 and relevant descriptions thereof. Further, the processing device 120 may adjust the treatment plan to adapt to the physiological motion of the subject based on the target physiological motion data, and the first physiological motion data and the second physiological motion data of each of the plurality of motion phases, e.g., by performing operation 1404.

It should be noted that the above description regarding the process 1700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1600 may be accomplished with one or more additional operations not described and/or without one or more of the operations discussed above. In some embodiments, a medical imaging device other than the MRI device (e.g., a PET scanner) may be configured to acquire scan data of the subject before the radiation treatment, which may be used to track the physiological motion of the subject during the radiation treatment.

Figure 18:
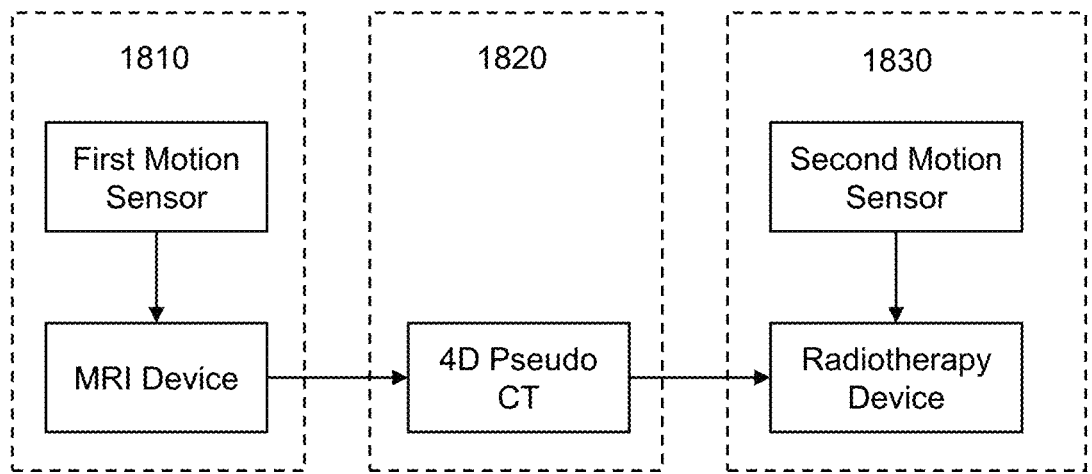
FIG. 18 is a schematic diagram illustrating an exemplary process for treating a subject according to some embodiments of the present disclosure.

FIG. 18 is a schematic diagram illustrating an exemplary process for treating a subject according to some embodiments of the present disclosure.

As shown in FIG. 18, process 1800 may include a preparation stage 1810, a treatment planning stage 1820, and a radiation treatment stage 1830.

In the preparation stage 1810, an MRI device may be directed to acquire obtain MRI data of a subject by performing an MRI scan on the subject, and a first motion sensor may be directed to acquire sensor data relating to a physiological motion of the subject during the MRI scan.

In the treatment planning stage 1820, a treatment plan may be generated based on the MRI data collected in the preparation stage 1810. For example, the processing device 120 may generate a pseudo CT image of the subject based on the MRI data, and further generate the treatment plan based on the pseudo CT image of the subject.

In the radiation treatment stage 1830, a radiotherapy device may be directed to deliver a radiation treatment to the subject according to the treatment plan, and a second motion sensor may be directed to collect target sensor data relating to the physiological motion of the subject during the radiation treatment. Further, the processing device 120 may adjust the treatment plan to adapt to the physiological motion of the subject during the radiation treatment based on the target sensor data, the MRI data, and the sensor data, for example, by performing operation 1704.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, radio frequency (RF), or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (Saas).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to surface modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system for radiation therapy, comprising:
at least one storage device including a set of instructions; and
at least one processor configured to communicate with the at least one storage device, wherein when executing the set of instructions, the at least one processor is configured to direct the system to perform operations including:

obtaining a plurality of sets of motion data each of which corresponds to one of a plurality of motion phases of a subject, a set of motion data corresponding to a motion phase including first physiological motion data and second physiological motion data reflecting a physiological motion during the motion phase, the first physiological motion data being collected via a medical imaging device, and the second physiological motion data being collected via a first motion sensor; and directing a radiotherapy device to deliver a radiation treatment to the subject according to a treatment plan, wherein during the radiation treatment, obtaining target physiological motion data reflecting the physiological motion of the subject during the radiation treatment, the target physiological motion data being collected via a second motion sensor;

determining, among the plurality of motion phases, a target motion phase of the subject based on the second physiological motion data corresponding to the plurality of motion phases and the target physiological motion data, the target motion phase being an estimated current motion phase of the subject; and adjusting the treatment plan to adapt to the physiological motion of the subject based on the target motion phase.

2. The system of claim 1, wherein the adjusting the treatment plan to adapt to the physiological motion of the subject based on the target motion phase comprises:

determining, based on the first physiological motion data corresponding to the target motion phase, position information of one or more regions of interest (ROIs) of the subject during the target motion phase; and directing the radiotherapy device to gate a delivery of a radiation beam or aim the radiation beam at a target of the subject according to the position information of the one or more ROIs.

3. The system of claim 1, wherein the obtaining a plurality of sets of motion data comprises:

obtaining scan data and sensor data of the subject that are simultaneously collected by the medical imaging device and the first motion sensor, respectively;

determining the first physiological motion data of the plurality of sets of motion data based on the scan data; and determining the second physiological motion data of the plurality of sets of motion data based on the sensor data.

4. The system of claim 3, wherein the scan data includes a plurality of sets of scan data each of which corresponds to one of the plurality of motion phases of the subject, and the determining the first physiological motion data of the plurality of sets of motion data based on the scan data comprises:

for each of the plurality of motion phases of the subject, reconstructing a medical image of the subject corresponding to the motion phase based on the set of scan data corresponding to the motion phase; and determining, based on the medical image corresponding to the motion phase, the first physiological motion data of the motion phase.

5. The system of claim 4, wherein the determining, based on the medical image corresponding to the motion phase, the first physiological motion data of the motion phase comprises:

determining a motion vector field between the motion phase and a reference motion phase among the plurality of motion phases based on the medical image corresponding to the motion phase and a medical image corresponding to the reference motion phase; and designating the motion vector field of the motion phase as the first physiological motion data of the motion phase.

6. The system of claim 3, wherein the treatment plan is generated based on the scan data of the subject.

7. The system of claim 1, wherein the first motion sensor includes at least one of a radar sensor, an optical sensor, a ranging device, a time-of-flight (TOF) device, a structured light scanner, a camera, a cardiac sensor, or a respiratory sensor.

8. The system of claim 1, wherein the medical imaging device includes at least one of a computed tomography (CT) device, a magnetic resonance imaging (MRI) device, or a positron emission tomography (PET) device.

9. The system of claim 1, wherein the second physiological motion data collected via the first motion sensor includes surface motion data reflecting a surface motion of the subject, the target physiological motion data collected via the second motion sensor includes target surface motion data reflecting the surface motion of the subject during the radiation treatment, and the surface motion is induced by the physiological motion of the subject.

10. The system of claim 9, wherein the adjusting the treatment plan to adapt to the physiological motion of the subject based on the target motion phase further comprises:

obtaining target rigid motion data reflecting a rigid motion of the subject during the radiation treatment;

correcting the target surface motion data based on the target rigid motion data; and adjusting the treatment plan to adapt to the physiological motion of the subject based on the target motion phase.

11. The system of claim 9, wherein the target motion phase is selected among the motion phases by comparing the target surface motion data with the surface motion data of each of the motion phases.

12. The system of claim 11, wherein the target motion phase is selected among the motion phases by:

determining a first respiratory waveform based on the surface motion data of the motion phases;

determining a second respiratory waveform based on the target surface motion data;

identifying a portion of the first respiratory waveform that is similar to the second respiratory waveform; and determining the target motion phase based on the identified portion of the first respiratory waveform.

13. A system for radiation therapy, comprising:

at least one storage device including a set of instructions; and at least one processor configured to communicate with the at least one storage device, wherein when executing the set of instructions, the at least one processor is configured to direct the system to perform operations including:

obtaining Magnetic Resonance Imaging (MRI) data and sensor data that are simultaneously collected via an MRI device and a first motion sensor during an MRI scan of the subject, respectively, the sensor data relating to a physiological motion of the subject during the MRI scan; and directing a radiotherapy device to deliver a radiation treatment to the subject according to a treatment plan, wherein during the radiation treatment, obtaining target sensor data relating to the physiological motion of the subject collected via a second motion sensor during the radiation treatment; and adjusting the treatment plan to adapt to the physiological motion of the subject by:

for each of a plurality of motion phases of the subject, determining, based on the MRI data, first physiological motion data reflecting the physiological motion of the subject during the motion phase; and determining, based on the sensor data, second physiological motion data reflecting the physiological motion of the subject during the motion phase;

determining, based on the target sensor data, target physiological motion data reflecting the physiological motion of the subject during the radiation treatment; and adjusting the treatment plan to adapt to the physiological motion of the subject based on the target physiological motion data, and the first physiological motion data and the second physiological motion data of each of the plurality of motion phases.

14. The system of claim 13, wherein the at least one processor is further configured to direct the system to perform the operations including:

generating, based on the MRI data, a pseudo computed tomographic (CT) image of the subject; and generating, based on the pseudo CT image of the subject, the treatment plan.

15. The system of claim 14, wherein the pseudo CT image is generated using a generative adversarial network (GAN) model.

16. The system of claim 13, wherein the adjusting the treatment plan to adapt to the physiological motion of the subject based on the target physiological motion data, and the first physiological motion data and the second physiological motion data of each of the plurality of motion phases comprises:

determining, among the plurality of motion phases, a target motion phase of the subject based on the second physiological motion data corresponding to the plurality of motion phases and the target physiological motion data, the target motion phase being an estimated current motion phase of the subject;

adjusting the treatment plan to adapt to the physiological motion of the subject based on the target motion phase.

17. The system of claim 16, wherein the adjusting the treatment plan to adapt to the physiological motion of the subject based on the target motion phase comprises:

determining, based on the first physiological motion data corresponding to the target motion phase, position information of one or more regions of interest (ROIs) of the subject during the target motion phase; and directing the radiotherapy device to gate a delivery of a radiation beam or aim the radiation beam at a target of the subject according to the position information of the one or more ROIs.

18. A system, comprising:

a medical imaging device configured to acquire scan data of a subject by performing a medical scan on the subject before a radiation treatment of the subject;

a first motion sensor configured to acquire sensor data relating to a physiological motion of the subject during the medical scan of the subject;

a radiotherapy device configured to deliver the radiation treatment to the subject according to a treatment plan;

a second motion sensor configured to acquire target sensor data relating to the physiological motion of the subject during the radiation treatment; and a processing device configured to adjust the treatment plan to adapt to the physiological motion of the subject during the radiation treatment by:

for each of a plurality of motion phases of the subject, determining, based on the MRI data, first physiological motion data reflecting the physiological motion of the subject during the motion phase; and determining, based on the sensor data, second physiological motion data reflecting the physiological motion of the subject during the motion phase;

determining, based on the target sensor data, target physiological motion data reflecting the physiological motion of the subject during the radiation treatment; and adjusting the treatment plan to adapt to the physiological motion of the subject based on the target physiological motion data, and the first physiological motion data and the second physiological motion data of each of the plurality of motion phases.

19. The system of claim 18, wherein the medical imaging device is a Magnetic Resonance Imaging (MRI) device.

20. The system of claim 18, wherein at least one of the first motion sensor or the second motion sensor is a radar sensor.

* * * * *